United States Patent
Burgess et al.

(10) Patent No.: US 6,586,467 B2
(45) Date of Patent: Jul. 1, 2003

(54) PREPARATION OF PHOSPHATASE INHIBITORS

(75) Inventors: Laurence E. Burgess, Boulder, CO (US); John J. Gaudino, Longmont, CO (US); Robert D. Groneberg, Boulder, CO (US); Mark H. Norman, Thousand Oaks, CA (US); Martha E. Rodriguez, Longmont, CO (US); Xicheng Sun, Superior, CO (US); Eli M. Wallace, Lyons, CO (US)

(73) Assignee: Array BioPharma Inc., Boulder, CO (US)

(*) Notice: Subject to any disclaimer, the term of this patent is extended or adjusted under 35 U.S.C. 154(b) by 49 days.

(21) Appl. No.: 09/899,654

(22) Filed: Jul. 5, 2001

(65) Prior Publication Data

US 2002/0040003 A1 Apr. 4, 2002

Related U.S. Application Data

(60) Provisional application No. 60/216,201, filed on Jul. 6, 2000.

(51) Int. Cl.⁷ .................. C07C 255/00; A61K 31/275
(52) U.S. Cl. .................. 514/522; 514/602; 558/413; 558/414; 564/84
(58) Field of Search .................. 558/413, 414; 564/84; 514/602, 522

(56) References Cited

U.S. PATENT DOCUMENTS 6,353,023 B1 * 3/2002 Larsen et al. .............. 514/533

FOREIGN PATENT DOCUMENTS

| WO | 9911606 | 3/1999 |
| WO | 0053583 | 9/2000 |

OTHER PUBLICATIONS

Elchebly, M., et al., *Science* 283:1544–1548, 1999.
Sarmiento, M., et al., *J. Med. Chem.* 43:146–155, 2000.
Wrobel, J., et al., *J. Med. Chem.* 42:3199–3202, 1999.
Norman, D.P.G., et al., *JOC* 64:9301–9306, 1999.
Bleasdale, J., et al., *Biochemistry*, 40:5642–5654, 2001.

* cited by examiner

*Primary Examiner*—Joseph K. McKane
*Assistant Examiner*—Kamal Saeed
(74) *Attorney, Agent, or Firm*—McDonnell Boehnen Hulbert & Berghoff

(57) ABSTRACT

Disclosed are compounds of the Formula I

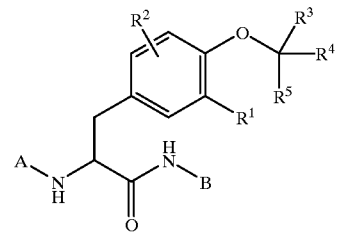

and pharmaceutically acceptable salts and prodrugs thereof, wherein A, B; $R^1$, $R^2$, $R^3$, $R^4$ and $R^5$ are as defined in the specification.

Such compounds are tyrosine phosphatase inhibitors and useful in the treatment or prevention of Type II Diabetes Mellitus. Also encompassed by the invention are formulations comprising the noted compounds, processes for preparing such compounds, a method for treating or preventing Type II Diabetes Mellitus.

16 Claims, No Drawings

PREPARATION OF PHOSPHATASE INHIBITORS

BACKGROUND OF THE INVENTION

This application claims benefit of application Ser. No. 60/216,201 filed Jul. 6, 2000.

FIELD OF THE INVENTION

This invention relates to the preparation of phosphatase inhibitors that act as phosphotyrosine mimetics. The invention particularly relates to compounds designed to inhibit protein-tyrosine phosphatase 1B, and for the treatment of diabetes.

SUMMARY OF THE RELATED ART

Protein tyrosine kinases (PTK) and protein tyrosine phosphatases (PTP) play an essential role in the regulation of various cellular functions including cell growth, proliferation, differentiation, metabolism and immune responses. They are therefore potentially important targets for therapeutic intervention in a number of diseases, including cancers and diabetes. PTKs generate phosphotyrosyl (pTyr) residues by mediating the phosphorylation of tyrosyl residues. PTPs, in turn, remove pTyr phophates and may play either positive or negative roles in cellular signal transduction.

At present, about 100 enzymes comprise the PTP family and each is either receptor-like or cytoplasmic. One such enzyme is PTP1B, a prototypic intracellular PTP that is expressed in many human tissues and is implicated as a negative regulator of insulin receptor signaling. Recent studies have shown that a correlation exists between levels of PTP1B and insulin resistance states, suggesting that PTP1B may play a role in the insulin resistance associated with diabetes and obesity. Apparently, PTP1B plays a vital role in the dephosphorylation of the insulin receptor. Further, a knockout study has revealed that mice lacking functional PTP1B exhibit increased sensitivity toward insulin and are resistant to obesity (Elchebly, M. et al., *Science* 1999, 283, 1544–1548). These studies suggest that PTP1B inhibitors would be useful in the treatment of insulin resistance and obesity. More importantly, such an inhibitor could function as an agent for the treatment of non-insulin dependent diabetes mellitus without inducing hypoglycemia.

To date, many of the previously reported PTP1B inhibitors have been peptide-based, containing negatively charged sulfate or phosphonic acid derivatives. Most of these compounds have been found to be inefficient in crossing cell membranes and are unstable in vivo. More recently, small organic molecules have been identified as potent and selective inhibitors of PTP1B (Larsen, S. et al. WO 00/53583; Larsen, S. et al., WO 99/11606; Sarmieto, M. et al., *J. Med. Chem.* 2000, 43, 146–155; Wrobel, J. et al., *J. Med. Chem.* 1999, 42, 3199–3202). Still desired is a PTP1B inhibitor that is even less peptidic in nature such that it increases solubility, absorption, cellular penetration and oral availability.

SUMMARY OF THE INVENTION

This invention provides certain tyrosine analogs of Formula I that are useful for treating Type II diabetes mellitus. Specifically, the present invention relates to compounds of Formula I that inhibit the protein tyrosine phosphatase 1B enzyme. Also provided are formulations containing compounds of Formula I and methods of using the compounds to treat a patient in need thereof. In addition, there are described processes for preparing the inhibitory compounds of Formula I.

The present invention relates to PTP1B inhibitors, pharmaceutically acceptable salts and prodrugs thereof useful in the therapeutic or prophylactic treatment of Type II diabetes mellitus. The invention also encompasses pharmaceutical compositions and methods for the treatment of Type II diabetes mellitus.

Accordingly, the compounds of the invention are members of the class of compounds of Formula I:

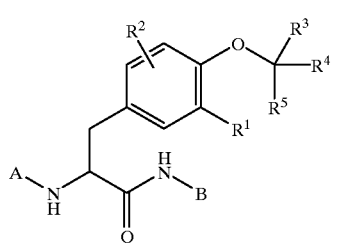

I wherein $R^1$ is selected from hydrogen, hydroxy, halogen, amino, monoalkylamino, trifluoromethyl, aminomethyl, cyano, nitro, —COOR$^6$, and
heteroaryl optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$;

$R^2$ is selected from hydrogen, hydroxy, halogen, lower alkyl, lower alkoxy, alkoxyalkyl, hydroxyalkyl, lower alkenyl, amino, mono- or dialkylamino, cyano, nitro, trifluromethyl, —CON(R$^6$)$_2$, —COOR$^6$, and
aryl and heteroaryl optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$;

$R^3$, $R^4$, $R^5$ are independently selected from hydrogen, hydroxy, halogen, lower alkyl, lower alkenyl, cycloalkyl, cyano, —CON(R$^6$)$_2$ and —COOR$^6$, and
aryl and heteroaryl optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$;

A is selected from lower alkyl, lower alkenyl, lower alkynyl, —C(O)R$^7$, —S(O)$_2$R$^7$, —C(O)NHR$^7$, —CO$_2$R$^7$, —(CH$_2$)$_n$S(O)$_q$R$^7$, —(CH$_2$)$_p$C(O)R$^7$, —(CH$_2$), $_p$C(O)NHR$^7$, —(CH$_2$)$_p$CO$_2$R$^7$, (CH$_2$)$_n$OR$^7$, and
aryl, heteroaryl, arylalkyl, and heteroarylalkyl, where the ring portion of each is optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$;

B is selected from hydrogen, lower alkyl, lower alkenyl, lower alkynyl, —(CH$_2$)$_n$S(O)$_q$R$^7$, —(CH$_2$)$_p$C(O)R$^7$, —(CH$_2$)$_p$C(O)NHR$^7$, —(CH$_2$)$_p$CO$_2$R$^7$, (CH$_2$)$_n$OR$^7$, and
aryl, heteroaryl, arylalkyl, arylalkenyl, arylalkynyl, heteroarylalkyl, heteroarylalkenyl and heteroarylalkynyl, where the ring portion of each is optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$;

n is 2–4;
p is 1–2;
q is 0–2;
R$^6$ is selected from hydrogen, lower alkyl, and lower alkenyl;
R$^7$ is selected from lower alkyl, or
aryl, heteroaryl, arylalkyl, and heteroarylalkyl, where the ring portion of each is optionally substituted with one, two or three groups independently selected from halogen, lower alkyl, hydroxy, amino, mono- or dialkylamino, trifluoromethyl, C(O)R$^8$, COOR$^8$, C(O)NHR$^8$, and OR$^8$; and
R$^8$ is independently selected from hydrogen, and
lower alkyl, aryl and heteroaryl optionally substituted with one, two or three groups independently selected from lower alkyl, halogen, lower alkoxy, hydroxy, amino, mono- or dialkylamino, and trifluoromethyl.

DETAILED DESCRIPTION OF THE INVENTION

The novel compounds encompassed by the instant invention are those described by the general Formula I set forth above, and the pharmaceutically acceptable salts and prodrugs thereof.

Preferred compounds of Formula I are those where R$^1$ is selected from hydroxy, amino, mono-C$_{1-2}$-alkylamino and —COOH; R$^2$ is hydrogen; R$^3$ is selected from hydrogen, fluoro and methyl; R$^4$ is selected from hydrogen and —COOH; R$^5$ is —COOH; A is selected from —C(O)R$^7$ and —S(O)$_2$R$^7$; B is selected from lower alkyl, aryl-C$_{2-6}$-alkyl, 5–6-membered heteroaryl-C$_{2-6}$-alkyl, and (CH$_2$)$_n$OR$^7$; R$^7$ is selected from aryl, 5–6 membered heteroaryl, aryl-C$_{1-3}$-alkyl, and heteroaryl-C$_{1-3}$-alkyl; n is 2–4; and R$^8$ is lower alkyl.

More preferred compounds of Formula I are those where R$^1$ is selected from hydroxy, amino, and monomethylamino; R$^2$ is hydrogen; R$^3$ is selected from hydrogen and fluoro; R$^4$ is hydrogen; R$^5$ is —COOH; A is selected from —C(O)R$^7$ and —S(O)$_2$R$^7$; B is selected from C$_{4-6}$-alkyl, phenyl-C$_{3-4}$-alkyl, 5–6 membered heteroaryl-C$_{3-4}$-alkyl, and (CH$_2$)$_n$OR$^7$; R$^7$ is selected from phenyl, 5–6 membered heteroaryl, phenyl-C$_{1-2}$-alkyl, and 5–6 membered heteroaryl-C$_{1-2}$-alkyl; n is 2–4; and R$^8$ is lower alkyl.

In addition to the compounds of Formula I, the invention encompasses compounds of Formula Ia:

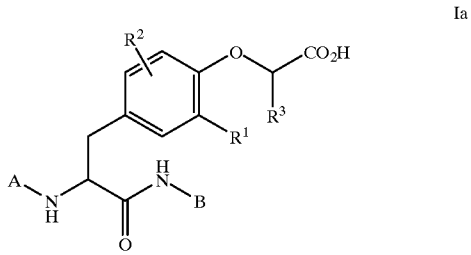

Ia wherein R$^1$, R$^2$, R$^3$, A and B are as defined above for Formula I.

Preferred compounds of Formula Ia are those where R$^1$ is selected from amino and hydroxy; R$^2$ is hydrogen; R$^3$ is selected from hydrogen, fluoro and methyl; A is selected from —C(O)R$^7$ and —S(O)$_2$R$^7$; B is selected from arylalkyl, heteroarylalkyl, and (CH$_2$)$_n$OR$^7$; R$^7$ is selected from aryl, heteroaryl, arylalkyl, and heteroarylalkyl; and n is 2–4.

In addition, the invention encompasses compounds of Formula Ib:

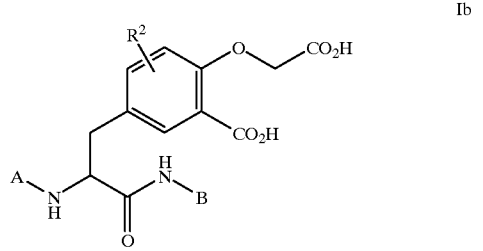

Ib wherein R$^2$, A and B are as defined above for Formula I.

Preferred compounds of Formula Ib are those where R$^2$ is hydrogen; A is selected from —C(O)R$^7$ and —S(O)$_2$R$^7$; B is selected from arylalkyl, heteroarylalkyl, and (CH$_2$)$_n$OR$^7$; R$^7$ is selected from aryl, heteroaryl, arylalkyl, and heteroarylalkyl; and n is 2–4.

Further, the invention encompasses compounds of Formula Ic:

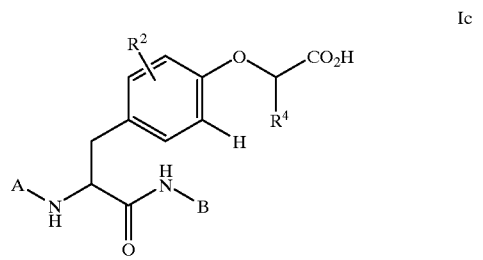

Ic wherein R$^2$, R$^4$, A and B are as defined above for Formula I.

Preferred compounds of Formula Ic are those where R$^2$ is hydrogen; R$^4$ is selected from —COOH and tetrazolyl; A is selected from —C(O)R$^7$ and —S(O)$_2$R$^7$; B is selected from arylalkyl, heteroarylalkyl, and (CH$_2$)$_n$OR$^7$; R$^7$ is selected from aryl, heteroaryl, arylalkyl, and heteroarylalkyl; and n is 2–4.

Except as expressly defined otherwise, the following definition of terms is employed throughout this specification.

By "alkyl" and "lower alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. More preferred alkyl radicals are C$_{1-3}$ alkyl.

By "alkoxy" and "lower alkoxy" in the present invention is meant straight or branched chain alkyl groups having 1–6 carbon atoms, attached through a divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy. More preferred are C$_{1-3}$ alkoxy.

By "alkylthio" and "lower alkylthio" in the present invention is meant straight or branched chain alkyl groups having 1–6 carbon atoms, attached through a divalent sulfur atom, such as, for example, methylthio, ethylthio, propylthio, isopropylthio, n-butylthio, sec-butylthio, tert-butylthio, pentylthio, isopentylthio, neopentylthio, hexylthio, and 3-methylpentylthio. More preferred are $C_{1-3}$ alkylthio.

"Alkenyl" means straight and branched hydrocarbon radicals having from 2 to 6 carbon atoms and at least one double bond and includes ethenyl, propenyl, 1-but-3-enyl, 1-pent-3-enyl, 1-hex-5-enyl and the like. More preferred are lower alkenyl having 3–5 carbon atoms.

"Alkynyl" means straight and branched hydrocarbon radicals having from 2 to 6 carbon atoms and one triple bond and includes ethynyl, propynyl, butynyl, pentyn-2-yl and the like. More preferred are alkynyl having 3–5 carbon atoms.

By the term "halogen" in the present invention is meant fluorine, bromine, chlorine, and iodine.

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. More preferred heteroaryl groups are 5-, or 6- membered radicals. Heteroaryl groups are optionally mono-, di-, or trisubstituted with, e.g., halogen, lower alkyl, lower alkoxy, lower alkylthio, haloalkyl, aryl, heteroaryl, and hydroxy.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, lower alkylthio, trifluoromethyl, aryl, heteroaryl, and hydroxy.

The terms "aralkyl" or "arylalkyl" means an alkyl moiety (as defined above) substituted with one or more aryl moiety (also as defined above). More preferred aralkyl radicals are aryl-$C_{1-3}$-alkyl. Examples include benzyl, phenylethyl, and the like.

The term "heteroarylalkyl" means an alkyl moiety (as defined above) substituted with an heteroaryl moiety (also as defined above). More preferred heteroarylalkyl radicals are 5- or 6-membered heteroaryl-$C_{1-3}$-alkyl. Examples include, oxazolemethyl, pyridylethyl and the like.

It is to be understood that in instances where two or more radicals are used in succession to define a substituent attached to a structure, the first named radical is considered to be terminal and the last named radical is considered to be attached to the structure in question. Thus, for example, for the formula —C(O)R$^7$ where R$^7$ is "alkylamino", the structure is —C(O)-NH-alkyl; similarly, if R$^7$ is "aminoalkyl" then the structure is —C(O)-alkyl-NH$_2$.

The following abbreviations are used interchin the application.

| dec | Decomposes |
| Dmp | Melting point |
| RT | Room temperature |
| THF | Tetrahydrofuran |
| TLC | Thin layer chromatography |
| HOAc | Acetic acid |
| HCO$_2$K | Potassium formate |
| PyBOP | Benzotriazol-1-yloxytripyrrolidinophosphonium hexafluorophosphate |
| CHCl$_3$ | Chloroform |
| CH$_2$Cl$_2$ | Methylene chloride |
| CBz | Carbobenzyloxy |
| Cbz-Cl | Benzyl chloroformate |
| CO | Carbon monoxide |

-continued

| DIEA | Diisopropylethylamine |
| DMF | N,N'-Dimethylformamide |
| DPPF | Diphenylphosphinoferrocene |
| DTT | Dithiothreitol |
| EDC | 1-(3-Dimethylaminopropyl)-3-ethylcarbodiimide hydrochloride |
| EDTA | Ethylenediaminetetraacetic acid (and salts) |
| EtOAc | Ethyl acetate |
| EtOH | Ethanol |
| Et$_2$O | Diethyl ether |
| HCl | Hydrochloric acid |
| H$_2$O$_2$ | Hydrogen peroxide |
| H$_2$SO$_4$ | Sulfuric acid |
| HOBT | 1-Hydroxybenzotriazole |
| KOH | Potassium hydroxide |
| CH$_3$CN | Acetonitrile |
| MgSO$_4$ | Magnesium sulfate |
| MeOH | Methanol |
| K$_2$CO$_3$ | Potassium carbonate |
| NaBH(OAc)$_3$ | Sodium triacetoxyborohydride |
| NaCl | Sodium chloride |
| NaOH | Sodium hydroxide |
| NaHCO$_3$ | Sodium bicarbonate |
| NaHMDS | Sodium hexamethyldisilazane |
| NaH | Sodium hydride |
| NBS | N-Bromosuccinimide |
| Pd/C | Palladium on carbon |
| Pd(OH)$_2$ | Palladium hydroxide (on carbon) |
| TEA | Triethylamine |
| TFA | Trifluoroacetic acid |
| Tris | Tris(hydroxymethyl)aminomethane |
| Boc | t-Butyloxycarbonyl |

"Pharmaceutically acceptable salt" as used herein refers to an organic or inorganic salt which is useful in the treatment of a warm-blooded animal. Such salts can be acid or basic addition salts, depending on the nature of the compound of Formula I. As used herein, "warm blooded animal" includes a mammal, including a member of the human, equine, porcine, bovine, murine, canine or feline species.

In the case of an acidic moiety in a compound of Formula I, a salt may be formed by treatment of a compound of Formula I with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of Formula I.

With respect to basic moieties, a salt is formed by the treatment of a compound of Formula I with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, D-glutamic, D-camphoric, glutaric, glycolic, phthalic, tartaric, lauric, stearic, salicyclic, methanesulfonic, benzenesulfonic, paratoluenesulfonic, sorbic, puric, benzoic, cinnamic and the like organic acids. An especially preferred salt of this type is a hydrochloride or sulfate salt of a compound of Formula I.

Also encompassed in the scope of the present invention are pharmaceutically acceptable esters of a carboxylic acid or hydroxyl containing group, including a metabolically labile ester or a prodrug form of a compound of Formula I. A metabolically labile ester is one that may produce, for example, an increase in blood levels and prolong the efficacy of the corresponding non-esterified form of the compound. A prodrug form is one that is not in an active form of the molecule as administered but which becomes therapeutically active after some in vivo activity or biotransformation, such as metabolism, for example, enzymatic or hydrolytic cleavage. Esters of a compound of Formula I, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_{1-4}$) alkyloxy) ethyl; for example, methoxyethyl, ethoxyethyl, propoxyethyl, isopropoxyethyl, etc.; 2-oxo-1,3-dioxolen-4-ylmethyl groups, such as 5-methyl-2-oxo-1,3,dioxolen-4-yl, etc.; $C_{1-3}$-alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the instant invention may have one or more asymmetrical carbon atoms and, therefore, may exist in stereoisomeric forms. All stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Additionally the present invention includes all possible tautomers thereof.

Further, the compounds of the invention may exist as crystalline solids which can be crystallized from common solvents such as EtOH, DMF, water, or the like. Thus, crystalline forms of the compounds of the invention may exist as solvates and/or hydrates of the parent compounds or their pharmaceutically acceptable salts. All of such forms likewise are to be construed as falling within the scope of the invention.

In another aspect, the compounds of the invention are useful for the therapeutic or prophylactic treatment of Type II diabetes mellitus. The compounds of the invention may be also be used as PTP1B inhibitory agents in other diseases, such as, for example, different type of cancers, insulin resistance and obesity. The term "cancer" includes, but is not limited to, the following cancers: breast, ovary, cervix, prostate, testis, esophagus, glioblastoma, neuroblastoma, stomach, skin, keratoacanthoma, lung, epidermoid carcinoma, large cell carcinoma, adenocarcinoma, bone, colon, adenocarcinoma, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkins, hairy cells, buccal cavity and pharynx (oral), lip, tongue, mouth, pharynx, small intestine, colon-rectum, large intestine, rectum, brain and central nervous system; and leukemia.

While it may be possible to administer a compound of the invention alone, normally it will be present as an active ingredient in a pharmaceutical formulation. Thus, in one another embodiment of the invention, there is provided a formulation comprising a compound of Formula I in combination, admixture, or associated with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilmans: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, eq. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery. Such forms of the compounds of the invention may be administered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

In a further embodiment of the invention, there is provided a pharmaceutical preparation for topical application comprising a compound of the invention, typically in concentrations in the range of from about 0.001% to about 10%, in combination with a pharmaceutically acceptable carrier, excipient, or diluent therefor. Such topical preparations can be prepared by combining the compound of the invention with conventional pharmaceutical diluents and carriers commonly used in topical dry, liquid, cream and aerosol formulations. Ointment and creams may be formulated, for example, with an aqueous or oily base with the addition of suitable thickening and/or gelling agents. Such bases may include water and/or an oil such as a liquid paraffin or a vegetable oil such as peanut oil or castor oil. Thickening agents which may be used according to the characteristics of the base may include, for example, soft paraffin, aluminum stearate, cetostearyl alcohol, propylene glycol, polyethylene glycols, woolfat, hydrogenated lanolin, beeswax, and the like.

Lotions may be formulated with an aqueous or oily base and will include also, in general, one or more of the following: stabilizing agents emulsifying agents, dispersing agents, suspending agents, thickening agents, coloring agents, perfumes, and the like. Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients such as antimicrobial agents, particularly antibiotics, anesthetics, analgesics and antipruritic agents.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include powders, tablets, pills, capsules and dragées.

The pharmaceutical formulations can be administered intravenously. Therefore, the invention further provides formulations for intravenous administration, which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, HCl, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Representative compounds of the present invention, which are encompassed by Formula I include, but are not limited to the compounds of the examples and their pharmaceutically acceptable acid or base addition salts or prodrugs thereof.

The examples presented below are intended to illustrate particular embodiments of the invention, and are not intended to limit the scope of the specification or the claims in any way.

An illustration of the preparation of compounds of the present invention is shown in Schemes 1–5. A, B, $R^1$, $R^2$, $R^3$, $R^4$ and $R^5$ are as described above for Formula I and X is a leaving group.

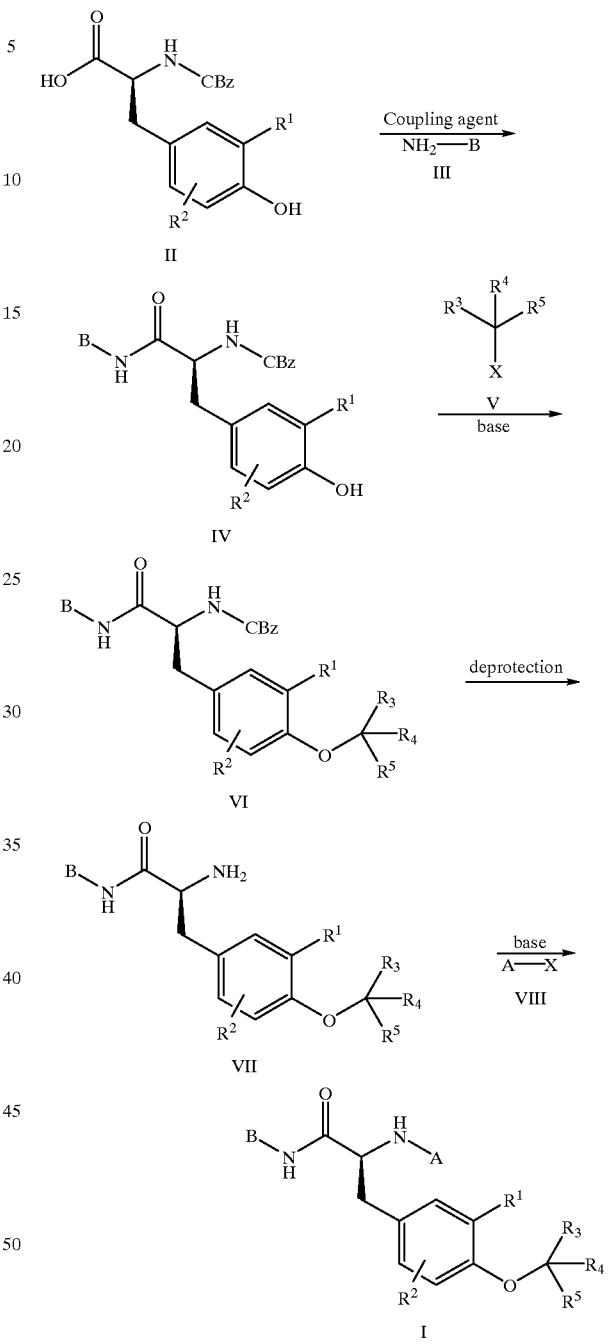

As shown in Scheme 1, an N-carbobenzyloxy tyrosine II can be subject to standard peptide coupling conditions, such as, EDC in the presence of an amine III to form the corresponding amide IV. The phenol of the amide IV can be alkylated with a group V that in the presence of a base such as KOH forms the ether VI. This compound can be deprotected using for example, catalytic hydrogenation, to yield the free amine VII. The amine VII can be alkylated with a halide VIII to afford a compound of the Formula I. A compound of Formula I may be interconverted within the definitions of $R^2$, $R^3$, $R^4$ or $R^5$ to provide related examples with the same generic Formula I. For example, when $R^5$ is carboxylate, it can be obtained from the corresponding ester or nitrile.

In certain embodiments of the invention, $R^1$ and/or $R^2$ have to be introduced onto the tyrosine-phenyl ring. For example, Scheme 2 depicts the synthetic route of compounds of the invention wherein $R^1$ is a carboxylate and is prepared from the corresponding halide.

Scheme 2

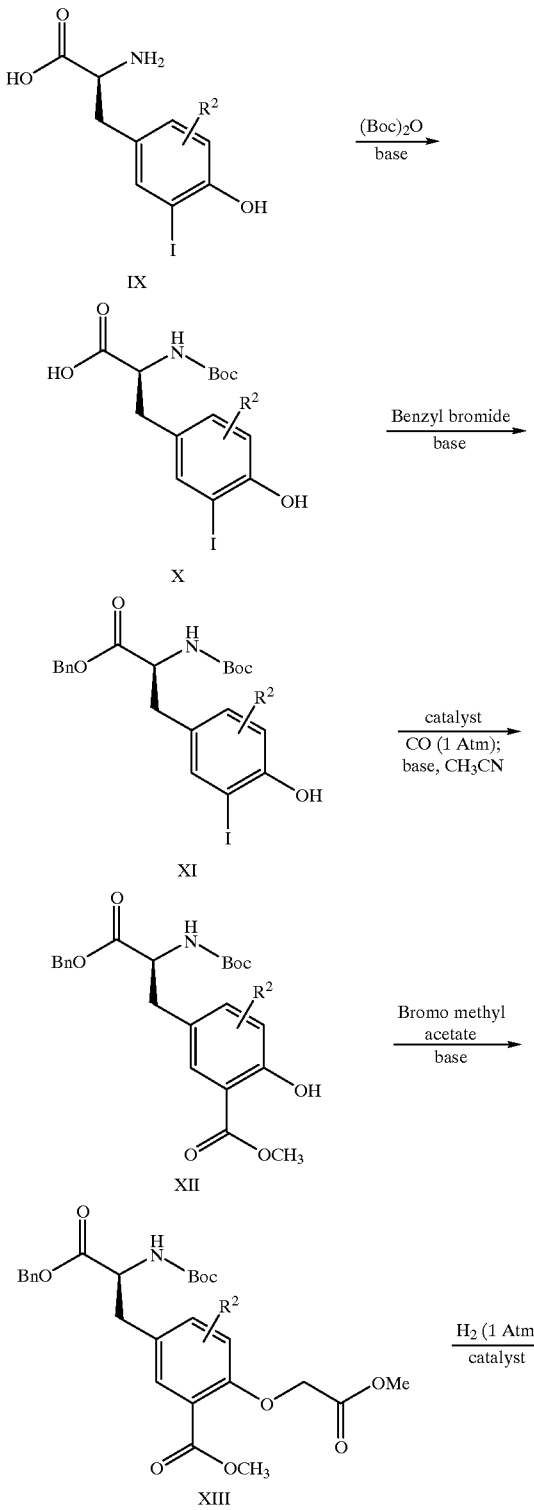

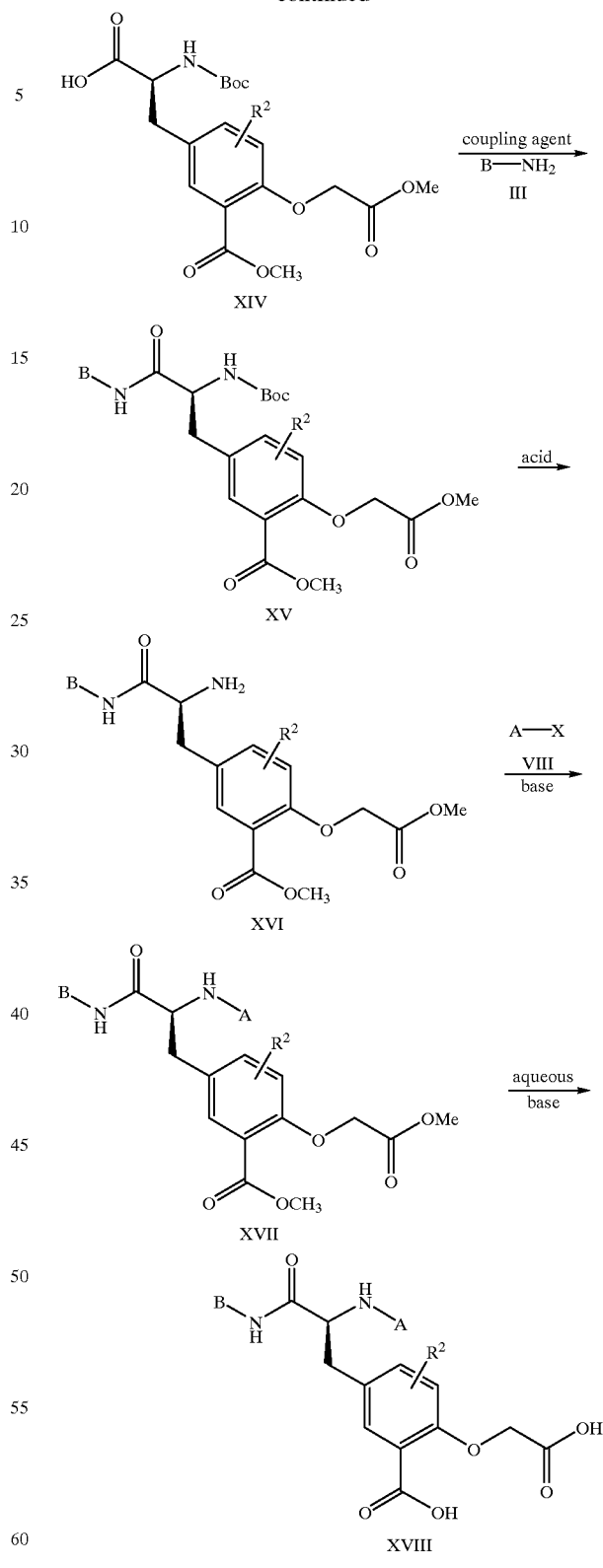

As shown in Scheme 2, the amine and acid groups of iodo tyrosine IX can be protected, respectively, to form X and then XI. The protected tyrosine XI can then be converted to the carboxylate XII by, for example, treatment with CO, acetonitrile, a base and a catalyst such as a palladium catalyst. The phenol of XII can be alkylated with, for example, bromomethyl acetate to form XIII, which can subsequently be deprotected to produce the free acid XIV. The free acid XIV can then be subjected to standard peptide coupling conditions, such as, for example, EDC in the presence of an amine III to form the corresponding amide XV. XV can be further deprotected to the amine XVI which in turn can be reacted with a halide VIII to yield XVII. XVII can then be hydrolized to form compound XVIII.

Additional embodiments are described wherein the tyrosine ring is functionalized with an aniline. For example, Scheme 3 depicts the synthesis of compounds of the structure shown below where $R^1=NH_2$ and $R^5=CO_2K$ Scheme 3

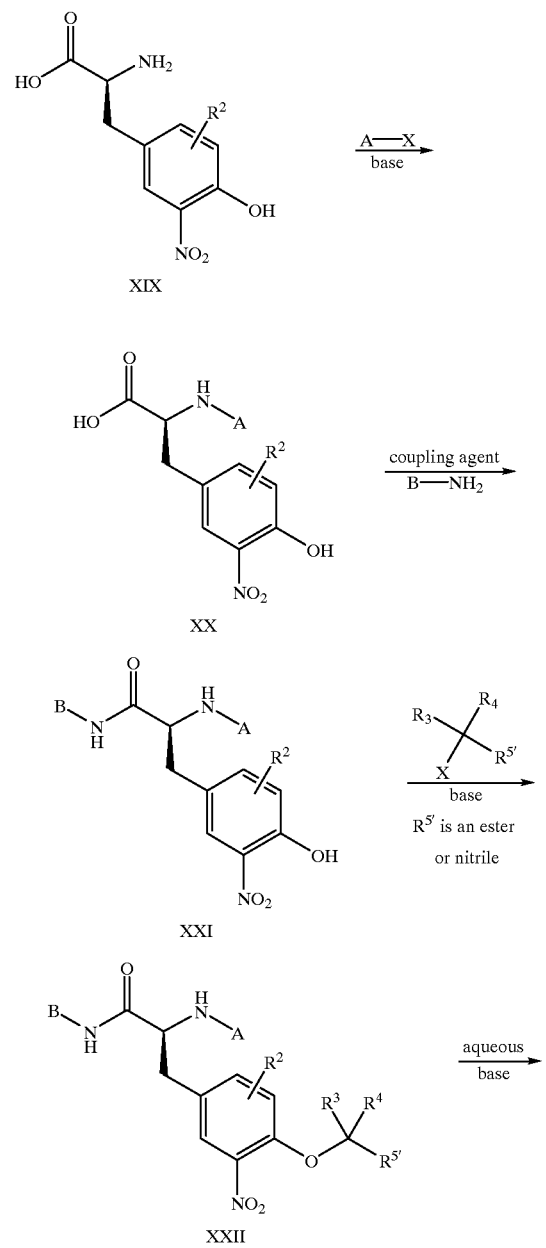

-continued

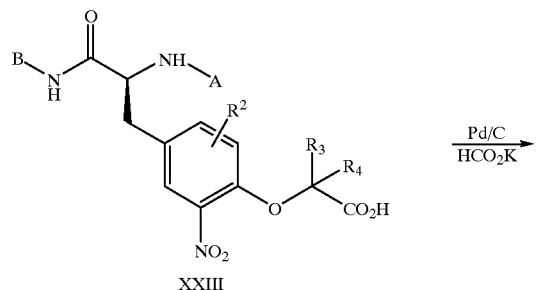

As shown in Scheme 3, derivatization of the free amino acid XIX with a reagent, A—X in the presence of a base can provide a compound of formula XX. Coupling using standard coupling agents, such as EDC, with an amine, B—NH2, can then provide XXI. Alklylation of the phenol can be accomplished with a group V that in the presence of a suitable base can form the ether XXII. Where $R^5$ is a nitrile or ester, aqueous hydrolysis can provie the acid XXIII. Reduction using catalytic hydrogenation with a metal such as palladium on carbon with hydrogen or phase transfer hydrogenation can provide the anilino carboxylate salt XXIV.

Additional embodiments are described wherein the tyrosine ring is functionalized with a phenol. For example, Scheme 4 depicts chemistry that can be used to generate compounds wherein $R^1=OH$, $R^5=CO_2H$ and $A=COR^7$.

Scheme 4

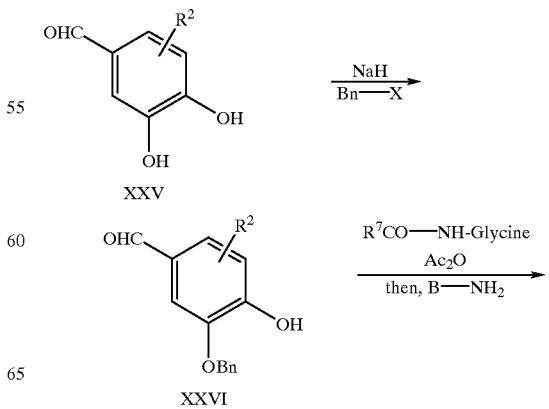

Scheme 5

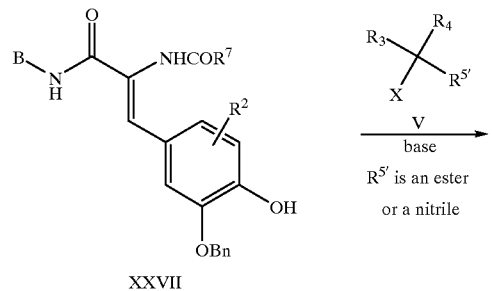

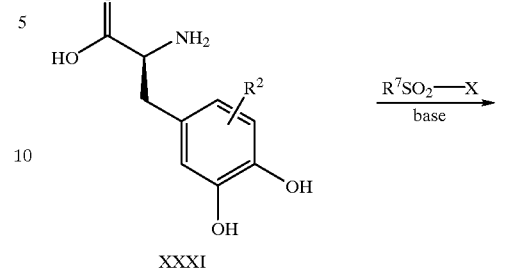

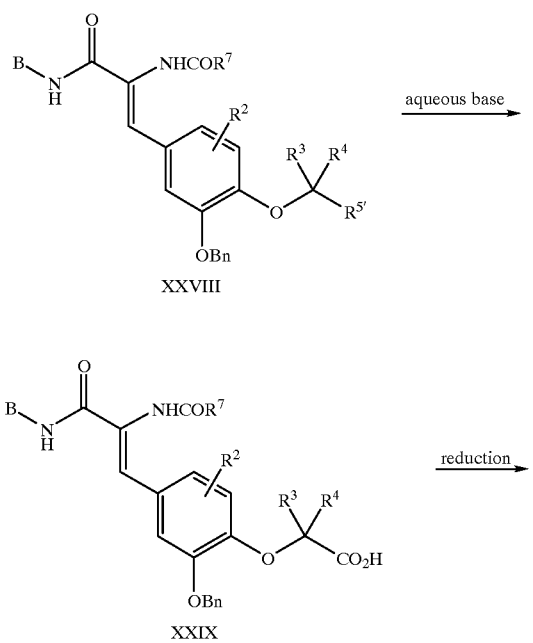

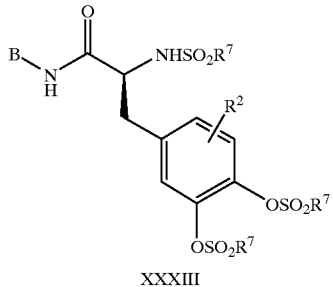

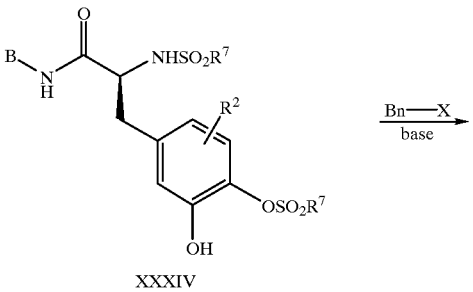

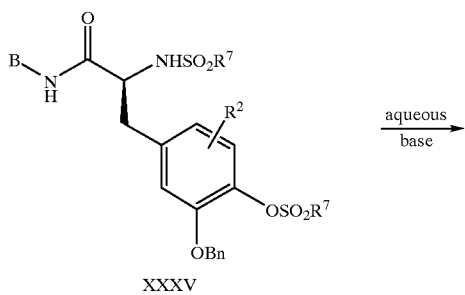

As shown in Scheme 4 selective protection of the diol XXV can be accomplished to provide phenol XXVI. Ehrylenmeyer condensation with an acid such as hippuric acid followed by the addition of an amine, B—NH$_2$, can provide a compound of formula XXVII. Alklylation of the phenol can be accomplished with a group V that in the presence of a suitable base can form the ether XXVIII. Where R$^5$ is a nitrile or ester, aqueous hydrolysis can provie the acid XXIX. Reduction using catalytic hydrogenation with a metal such as palladium on carbon with hydrogen or phase transfer hydrogenation can provide the phenol carboxylic acid XXX.

Scheme 5 depicts chemistry that can be used to generate compounds wherein R$^1$=OH, R$^5$=CO$_2$H and A=SO$_2$R$^7$.

17

-continued

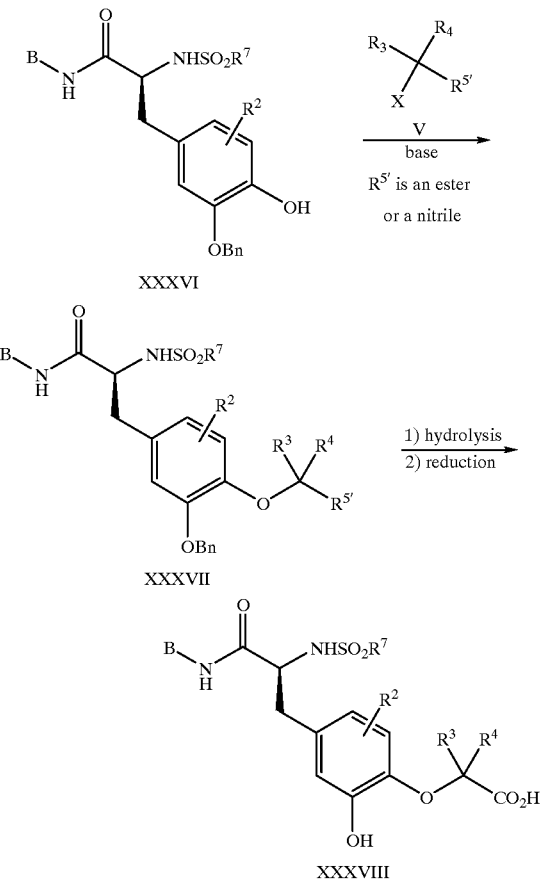

XXXVI

XXXVII

XXXVIII

As shown in Scheme 5 persulfonylation of a compound of formula XXXI can provide a compound of formula XXXII. Amide bond formation using standard coupling conditions such as EDC in the presence of an amine, B—NH$_2$, can provide an amide XXXIII. Partial deprotection can provide regiomeric mixture of phenols of formula XXXIV. Benzyl protection followed by basic hydrolysis can provide a phenol of formula XXXVI. Alklylation of the phenol can be accomplished with a group V that in the presence of a suitable base can form the ether XXXVII. Where R$^5$ is a nitrile or ester, aqueous hydrolysis followed by reduction using catalytic hydrogenation can provide the phenol carboxylic acid XXXVIII.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

18

EXAMPLES

Example 1

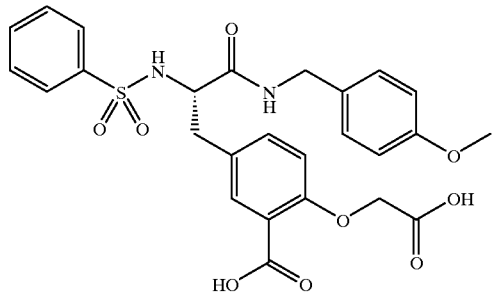

1

5-[(2S)-2-Benzenesulfonylamino-2-(4-methoxy-benzylcarbamoyl)-ethyl]-2-carboxymethoxy-benzoic acid (compound 1)

Step A: (2S)-2-tert-Butoxycarbonylamino-3-(4-hydroxy-3-iodo-phenyl)-propionic acid Iodotyrosine (10 g, 33 mmol) is stirred in dioxane (100 mL) at 0° C. 0.5 M NaOH (100 mL) is added and the mixture is stirred rapidly. Boc anhydride (7.8 g, 36 mmol) is added and the reaction is allowed to slowly warm to RT over 2 hours. The reaction becomes completely homogenous at this time. The dioxane is removed by concentration in vacuo and the aqueous solution extracted with EtOAc (2×100 mL). The aqueous solution is acidified to pH 3 with concentrated HCl. The mixture is extracted with EtOAc (2×100 mL) and the combined organics are washed with H$_2$O (200 mL) and saturated NaCl (200 mL). The organics are dried (MgSO$_4$), filtered, and concentrated to provide 2-tert-butoxycarbonylamino-3-(4-hydroxy-3-iodo-phenyl)-propionic acid.

Step B: (2S)-2-tert-Butoxycarbonylamino-3-(4-hydroxy-3-iodo-phenyl)-propionic acid benzyl ester (2S)-2-tert-Butoxycarbonylamino-3-(4-hydroxy-3-iodo-phenyl)-propionic acid (490 mg. 1.2 mmol) of Step A is stirred in EtOAc (3.6 mL) with DIEA (418 μL, 2.4 mmol) at RT under N$_2$. Benzyl bromide (171 μL, 1.44 mmol) is then added and the reaction mixture is then heated to 90° C. overnight. TLC in 3/1 hexane/EtOAc shows complete consumption of starting material (ninhydrin positive) and the appearance of two higher rf spots. The reaction is cooled to RT, diluted with EtOAc and washed with 1N HCl (2×30 mL) and with saturated NaHCO$_3$ (2×30 mL). The organics are dried (MgSO$_4$), filtered and concentrated to provide a mixture of mono- and dibenzylated products. Flash chromatography (3:1 hexane/EtOAc) affords the title compound, (2S)-2-tert-butoxycarbonylamino-3-(4-hydroxy-3-iodo-phenyl)-propionic acid benzyl ester.

Step C: 5-((2S)-2-Benzyloxycarbonyl-2-tert-butoxycarbonylamino-ethyl)-2-hydroxy-benzoic acid methyl ester (2S)-2-tert-Butoxycarbonylamino-3-(4-hydroxy-3-iodo-phenyl)-propionic acid benzyl ester (340 mg, 0.68 mmol) of Step B is stirred in 2.1 ml acetonitrile at RT under N$_2$. DPPF (23 mg, 0.042 mmol) is added followed by palladium acetate (5.0 mg, 0.022 mmol), TEA (190 uL, 1.37 mmol) and MeOH (440 uL). The solution is put through a vacuum/purge cycle 3 times with CO gas and then held under 1 atmosphere CO in a balloon. The solution is warmed to 68° C. After stirring overnight, TLC in 3/1 hexane EtOAc shows near complete consumption of starting material. The reaction is cooled to RT, concentrated in vacuo and purified by flash column chromaotgraphy (4:1 hexane/EtOAc) to provide 5-((2S)-2-benzyloxycarbonyl-2-tert-butoxycarbonylamino-ethyl)-2-hydroxy-benzoic acid methyl ester.

Step D: 5-((2S)-2-Benzyloxycarbonyl-2-tert-butoxycarbonylamino-ethyl)-2-methoxycarbonylmethoxy-benzoic acid methyl ester 5-((2S)-2-Benzyloxycarbonyl-2-tert-butoxycarbonylamino-ethyl)-2-hydroxy-benzoic acid methyl ester of Step C (213 mg, 0.49 mmol) is stirred in acetone (2 mL) with powdered $K_2CO_3$ (207 mg, 1.5 mmol) and bromomethyl acetate (95uL, 1.5 mmol) at RT under $N_2$ and then at 50° C. The reaction is diluted with EtOAc (100 mL) and washed with 1N HCl (30 mL) and saturated $NaHCO_3$ (2×30 mL). The organics are dried ($MgSO_4$), filtered, concentrated and purified by flash column chromatography to provide 5-((2S)-2-benzyloxycarbonyl-2-tert-butoxycarbonylamino-ethyl)-2-methoxycarbonylmethoxy-benzoic acid methyl ester.

Step E: 5-((2S)-2-tert-Butoxycarbonylamino-2-carboxy-ethyl)-2-methoxycarbonylmethoxy-benzoic acid methyl ester 5-((2S)-2-Benzyloxycarbonyl-2-tert-butoxycarbonylamino-ethyl)-2-methoxycarbonylmethoxy-benzoic acid methyl ester of Step D (135 mg, 0.27 mmol) is stirred in 95% EtOH (3 mL) with Pearlman's catalyst (palladium hydroxide on carbon) (70 mg) and put through a vacuum/purge cycle 3 times with $H_2$ gas. The reaction is then held under 1 atm of $H_2$ overnight. The catalyst is then filtered off on GF/F filter paper and the filtrate concentrated to provide 5-((2S)-2-tert-butoxycarbonylamino-2-carboxy-ethyl)-2-methoxycarbonylmethoxy-benzoic acid methyl ester which is used without further purification.

Step F: 5-[(2S)-2-tert-Butoxycarbonylamino-2-(4-methoxy-benzylcarbamoyl)-ethyl]-2-methoxycarbonylmethoxy-benzoic acid methyl ester 5-((2S)-2-tert-Butoxycarbonylamino-2-carboxy-ethyl)-2-methoxycarbonylmethoxy-benzoic acid methyl ester of Step F (51 mg, 0.12 mmol) is stirred in $CH_2Cl_2$ (1.2 mL) at 0° C. under $N_2$. EDC (24 mg, 0.12 mmol) is added and the reaction mixture is stirred for and additional 10 minutes. 4-Methoxybenzyl amine (0.18 μl, 0.14 mmol) is then added and the reaction is allowed to warm to RT overnight. The reaction is diluted with $CH_2Cl_2$ (25 mL) and is subsequently washed with 2N HCl (2×25 mL) and then saturated $NaHCO_3$ (2×25 mL). The organics are then dried over $MgSO_4$, filtered and and purified by flash column chromatography to provide 5-[(2S)-2-tert-butoxycarbonylamino-2-(4-methoxy-benzylcarbamoyl)-ethyl]-2-methoxycarbonylmethoxy-benzoic acid methyl ester.

Step G: 5-[(2S)-2-Amino-2-(4-methoxy-benzylcarbamoyl)-ethyl]-2-methoxycarbonylmethoxy-benzoic acid methyl ester 5-[(2S )-2-tert-Butoxycarbonylamino-2-(4-methoxy-benzylcarbamoyl)-ethyl]-2-methoxycarbonylmethoxy-benzoic acid methyl ester Step F (53 mg, 0.10 mmol) is dissolved in $CH_2Cl_2$ (1.5 mL) and TFA (0.5 mL) is added. The reaction is allowed to stir 4 h and is then concentrated in vacuo to afford the TFA salt of 5-[(2S)-2-amino-2-(4-methoxy-benzylcarbamoyl)-ethyl]-2methoxycarbonylmethoxy-benzoic acid methyl ester which is used without further purification.

Step H: 5-[(2S)-2-Benzenesulfonylamino-2-(4-methoxy-benzylcarbamoyl)-ethyl]-2-methoxycarbonylmethoxy-benzoic acid methyl ester 5-[(2S)-2-Amino-2-(4-methoxy-benzylcarbamoyl)-ethyl]-2-methoxycarbonylmethoxy-benzoic acid methyl ester of Step G (40 mg, 0.072 mmol) is stirred in pyridine (0.5 mL) at 0° C. under $N_2$. Benzenesulfonyl chloride (20 mg, 0.11 mmol) is added and the reaction is stirred overnight at RT. The mixture is then diluted with $CH_2Cl_2$ (20 mL), washed with 2N HCl (2×20 mL) and then with saturated $NaHCO_3$ (2×20 mL). The organics are dried over $MgSO_4$, filtered, concentrated and purified by flash column chromatography to provide 5-[(2S)-2-benzenesulfonylamino-2-(4-methoxy-benzylcarbamoyl)-ethyl]-2-methoxycarbonylmethoxy-benzoic acid methyl ester.

Step I: 5-[(2S)-2-Benzenesulfonylamino-2-(4-methoxy-benzylcarbamoyl)-ethyl]-2-carboxymethoxy-benzoic acid 5-[(2S)-2-Benzenesulfonylamino-2-(4-methoxy-benzylcarbamoyl)-ethyl]-2-methoxycarbonylmethoxy-benzoic acid methyl ester Step H (17 mg, 0.30 mmol) is stirred in 3:2 $THF/H_2O$ (3 mL) at RT. Lithium hydroxide monohydrate (20 mg, 0.5 mmol) is added and the reaction is stirred overnight. The mixture is partitioned between EtOAc (15 mL) and 2N HCl (15 mL). The organics are washed with saturated NaCl (1×15 mL), filtered and concentrated to afford the title compound (compound 1), 5-[(2S)-2-benzenesulfonylamino-2-(4-methoxy-benzylcarbamoyl)-ethyl]-2-carboxymethoxy-benzoic acid; $^1H$ NMR (400 MHz, $CDCl_3$) δ7.65 (d, 2H), 7.51 (m, 1H), 7.38 (m, 3H), 7.20 (d, 1H), 7.01 (d, 2H), 6.80 (d, 2H), 6.68 (d, 1H), 4.73 (s, 2H), 4.17 (m, 2H), 3.94 (m, 1H), 3.78 (s, 3H), 2.99 (dd, 1H), 2.91 (dd, 1H); MS (ES−) m/z 541 (M−1).

The following compounds can be prepared using similar chemistry to that which is described above:

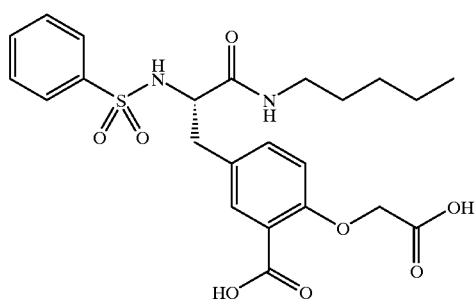

2

5-((2S)-2-Benzenesulfonylamino-2-pentylcarbamoyl-ethyl)-2-carboxymethoxy-benzoic acid (compound 2)

$^1$H NMR (400 MHz, CDCl$_3$) δ7.71 (s, 1H,), 7.63 (d, 2H), 7.47 (t, 1H), 7.38 (t, 2H, 7.24 (dd, 1H), 7.08 (m, 1H), 6.77 (d, 1H), 4.75 (s, 2H), 3.92 (m, 1H), 3.01 (m, 3H), 2.78 (m, 1H), 1.33 (m, 2H),1.27 (m, 2H), 1.19 (m, 2H), 0.84 (t, 3H); MS (ES−) m/z 491 (M−1).

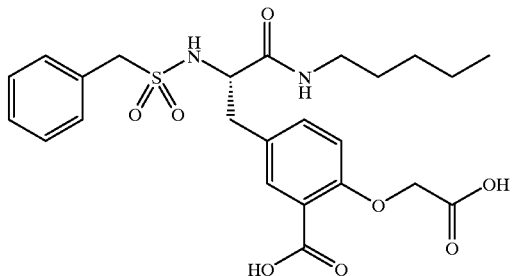

2-Carboxymethoxy-5-((2S)-2-pentylcarbamoyl-2-phenylmethanesulfonylamino-ethyl)-benzoic acid (compound 3)

$^1$H NMR (400 MHz, CDCl$_3$) δ;7.79 (s, 1H), 7.40–7.28 (m, 6H), 7.19 (m, 1H), 6.92 (d, 1H); 4.76 (s, 2H), 4.11 (dd, 2H), 3.38 (m, 1H), 3.10 (m, 2H), 2.96 (m, 1H), 2.83 (m, 1H), 1.37 (m, 2H), 1.23 (m, 2H), 1.19 (m, 2H), 0.83 (t, 3H); MS (ES−) m/z 505 (M−1).

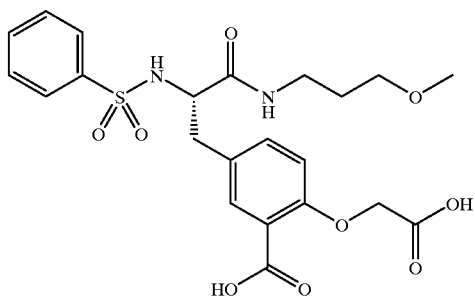

5-[(2S)-2-Benzenesulfonylamino-2-(3-methoxy-propylcarbamoyl)-ethyl]-2-carboxymethoxy-benzoic acid (compound 4)

$^1$NMR (400 MHz, CDCl$_3$) δ;7.64 (d, 2H), 7.62 (s, 1H), 7.50 (t, 1H), 7.37 (t, 2H), 7.23 (d, 1H), 6.76 (d, 1H), 4.75 (s, 2H), 3.88 (m, 1H), 3.37 (m, 1H), 3.34 (s, 3H) 3.18 (m, 1H), 2.87 (ddd, 2H), 1.62 (dd, 2H); MS (ES−) m/z 493 (M−1).

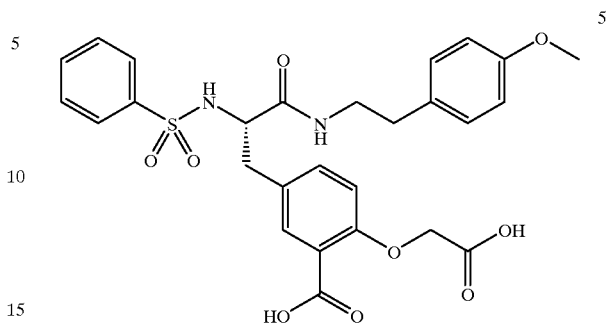

5-{(2S)-2-Benzenesulfonylamino-2-[2-(4-methoxy-phenyl)-ethylcarbamoyl]-ethyl}-2-carboxymethoxy-benzoic acid (compound 5)

$^1$H NMR (400 MHz, CDCl$_3$) δ;7.62 (m, 3H), 7.49 (m, 1H), 7.38 (m 2H), 7.20 (d, 1H), 7.10 (m, 1H), 7.04 (d, 2H), 6.83 (d, 2H), 6.73 (d, 1H), 4.73 (s, 2H), 3.84 (m, 1H), 3.78 (s, 3H), 3.28 (m, 2H), 2.83 (ddd, 2H), 2.60 (m, 1H); MS (ES−) m/z 551 (M−1).

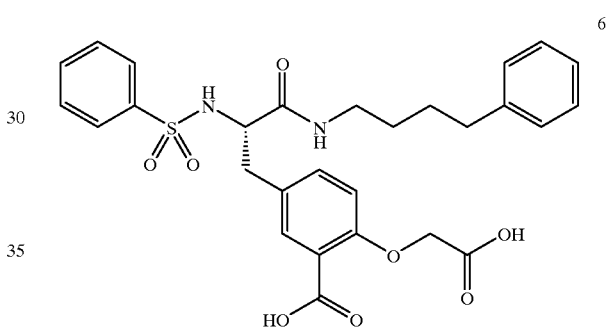

5-[(2S )-2-Benzenesulfonylamino-2-(4-phenyl-butylcarbamoyl)-ethyl]-2-carboxymethoxy-benzoic acid (compound 6)

$^1$H NMR (400 MHz, CDCl$_3$) δ;7.70 (s, 1H), 7.61 (d, 2H), 7.43 (m, 1H), 7.36–7.08 (m, 9H), 6.72 (d, 1H), 4.68 (s, 2H), 3.92 (m, 1H), 3.05 (m, 2H), 2.89 (ddd, 2H), 2.57 (m, 2H), 1.53 (m, 2H), 1.37 (m, 2H); MS (ES−) m/z 554 (M−1).

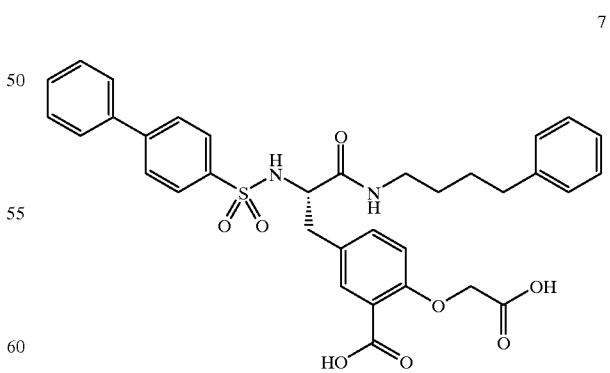

5-[(2S)-2-(Biphenyl-4-sulfonylamino)-2-(4-phenyl-butylcarbamoyl)-ethyl]-2-carboxymethoxy-benzoic acid (compound 7)

$^1$H NMR (400 MHz, CDCl$_3$) δ7.77 (s, 1H), 7.65 (d, 2H), 7.58 (m, 4H), 7.44 (m, 2H), 7.40 (m, 1H), 7.22 (m, 3H), 7.16

(m, 2H), 7.12 (m, 2H), 6.60 (d, 1H), 4.43 (dd, 2H), 3.95 (m, 1H), 3.08 (m, 2H), 2.91 (ddd, 2H), 2.52 (m, 2H), 1.50 (m, 2H), 1.39 (m, 2H).

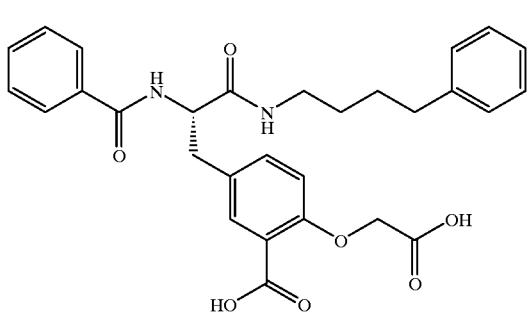

5-[(2S)-2-Benzoylamino-2-(4-phenyl-butylcarbamoyl)-ethyl]-2-carboxymethoxy-benzoic acid (compound 8)

$^1$H NMR (400 MHz, CDCl$_3$) δ;7.95 (s, 1H), 7.76 (d, 2H), 7.51 (m, 1H), 7.41 (m, 4H), 7.23 (m, 2H), 7.16 (m, 3H), 6.84 (d, 1H), 4.77 (m, 1H), 4.67 (s, 2H), 3.17 (m, 2H), 3.10 (ddd, 2H), 2.59 (m, 2H), 1.56 (m, 2H), 1.44 (m, 2H); MS (ES−) m/z 517 (M−1).

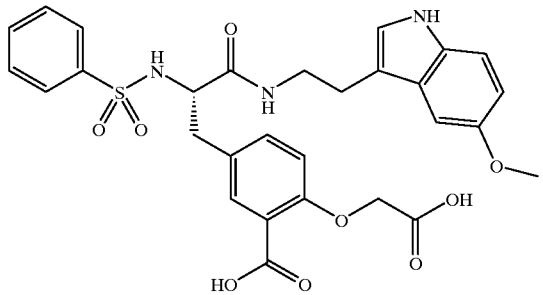

5-{(2S)-2-Benzenesulfonylamino-2-[2-(5-methoxy-1H-indol-3-yl)-ethylcarbamoyl]-ethyl}-2-carboxymethoxy-benzoic acid (compound 9)

$^1$H NMR (400 MHz, CDCl$_3$) δ7.59 (m, 3H), 7.43 (m, 1H), 7.31 (m, 2H), 7.26 (d, 1H), 7.16 (m, 2H), 6.96 (d, 2H), 6.82 (d, 1H), 6.61 (d, 1H), 4.64 (s, 2H), 3.82 (s, 3H), 3.39 (m, 2H), 2.80 (ddd, 2H), 2.79 (m, 1H); MS (ES−) m/z 594 (M−1).

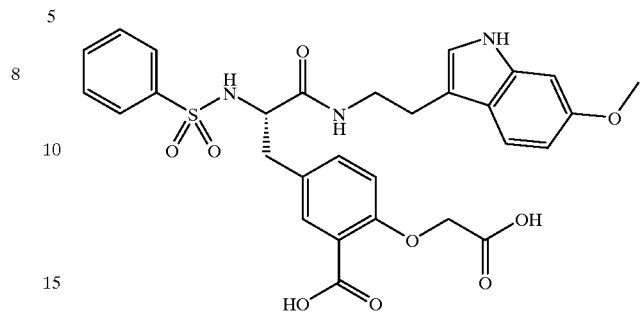

5-{(2S)-2-Benzenesulfonylamino-2-[2-(6-methoxy-1H-indol-3-yl)-ethylcarbamoyl]-ethyl}-2-carboxymethoxy-benzoic acid (compound 10)

$^1$H NMR (400 MHz, CDCl$_3$) δ7.60 (m, 3H), 7.44 (m, 1H), 7.38 (m, 2H), 7.16 (d, 1H), 7.03 (m, 1H), 6.84 (m, 2H), 6.76 (d, 1H), 6.61 (d, 1H), 4.63 (s, 2H), 3.87 (m, 1H), 3.81 (s, 3H), 3.36 (m, 2H), 2.80 ddd, 2H), 2.77 (m, 1H); MS (ES−) m/z 594 (M−1).

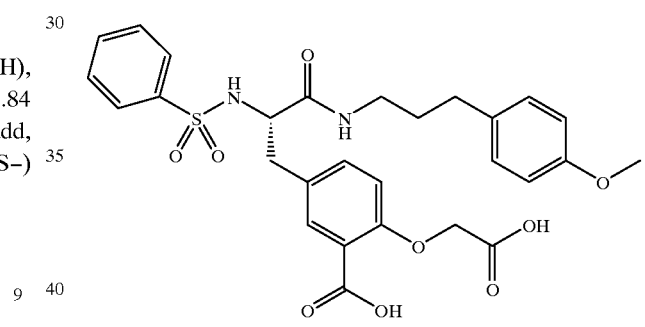

5-{(2S)-2-Benzenesulfonylamino-2-[3-(4-methoxy-phenyl)-propylcarbamoyl]-ethyl}-2-carboxymethoxy-benzoic acid (compound 11)

$^1$H NMR (400 MHz, MeOH-d$_3$) δ7.89 (t, 1H), 7.70–7.62 (m, 3H), 7.55–7.38 (m, 3H), 7.25 (dd, 1H), 7.09–7.01 (d, 2H), 6.87 (d, 1H), 6.80 (d, 2H), 4.72 (s, 2H), 3.92 (t, 1H), 3.78 (s,3H), 3.15–2.62 (m, 4H), 2.38 (t, 2H), 1.54 (q, 2H); MS (ES−) m/z 569.1 (M−1).

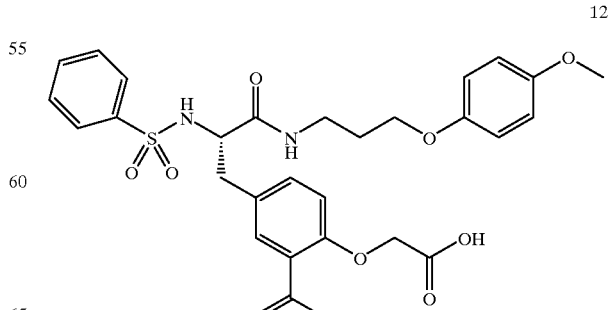

5-{(2S)-2-Benzenesulfonylamino-2-[3-(4-methoxy-phenoxy)-propylcarbamoyl]-ethyl}-2-carboxymethoxy-benzoic acid (compound 12)

$^1$H NMR (400 MHz, MeOH-d$_3$) δ7.99 (t, 1H), 7.66–7.60 (m, 4H), 7.53–7.38 (m, 4H), 7.24 (dd, 1H), 6.88–6.86 (m, 3H), 4.71 (s, 2H), 3.87 (t, 1H), 3.78–3.61 (m, 5H), 3.23–2.98 (m, 2H), 2.90 (dd, 1H), 2.72 (dd, 1H), 1.70 (q, 2H); MS (ES−) m/z 585.1 (M−1).

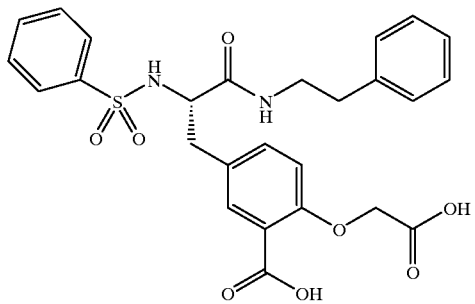

5-((2S)-2-Benzenesulfonylamino-2-phenethylcarbamoyl-ethyl)-2-carboxymethoxy-benzoic acid (compound 13)

MS (ES−) m/z 525.0 (M−1).

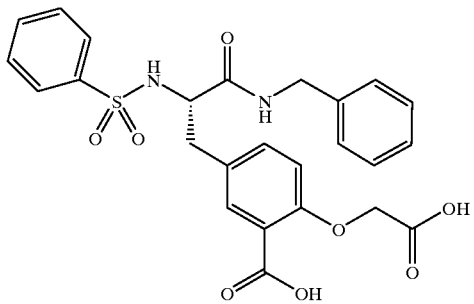

5-[(2S)-2-Benzenesulfonylamino-2-(3-phenyl-propylcarbamoyl)-ethyl]-2-carboxymethoxy-benzoic acid (compound 14)

MS (ES−) m/z 539.0 (M−1).

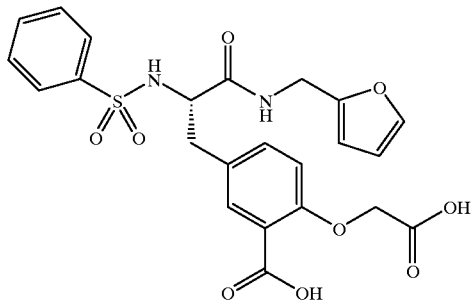

5-{(2S)-2-Benzenesulfonylamino-2-[(furan-2-ylmethyl)-carbamoyl]-ethyl}-2-carboxymethoxy-benzoic acid (compound 15)

MS (ES−) m/z 501.3 (M−1).

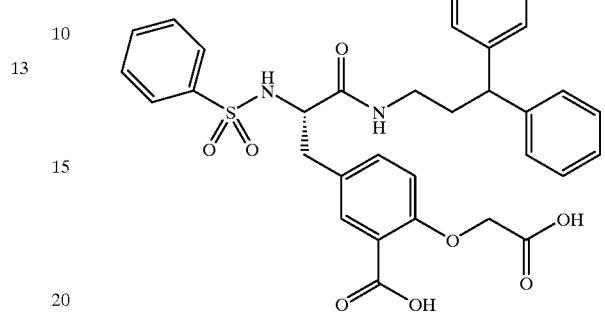

5-[(2S)-2-Benzenesulfonylamino-2-(3,3-diphenyl-propylcarbamoyl)-ethyl]-2-carboxymethoxy-benzoic acid (compound 16)

MS (ES−) m/z 615.1 (M−1).

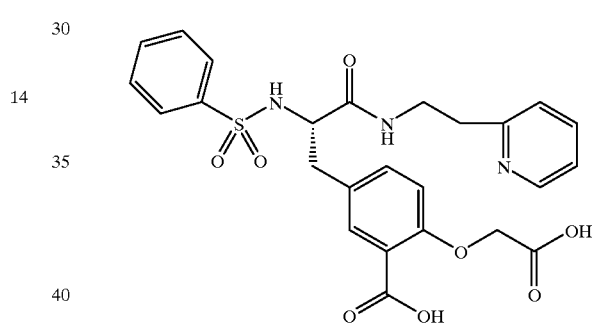

5-[(2S)-2-Benzenesulfonylamino-2-(2-pyridin-2-yl-ethylcarbamoyl)-ethyl]-2-carboxymethoxy-benzoic acid (compound 17)

MS (ES−) m/z 526.2 (M−1).

Example 2

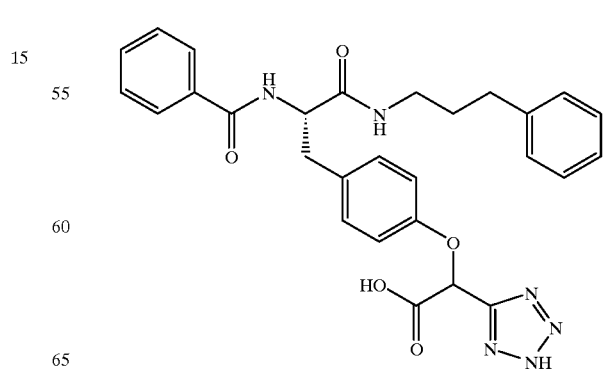

{4-[(2S)-2-Benzoylamino-2-(4-phenyl-butylcarbamoyl)-ethyl]-phenoxy}-(2H-tetrazol-5-yl)-acetic acid (compound 18)

Step A: (2S)-N-[2-(4-Hydroxy-phenyl)-1-(4-phenyl-butylcarbamoyl)-ethyl]-benzamide Phenyl butyl amine (0.55 mL, 3.51 mmol) is added to a stirred solution of N-benzoyl-L-tyrosine (1.00 g, 3.51 mmol), PyBop (2.19 g, 4.21 mmol) and Hunig's base (0.73 mL, 4.21 mmol) in DMF (10 mL) at RT under $N_2$. After 1 h, the reaction is diluted with EtOAc and the organic layer is washed with 10% HCl, water, saturated $NaHCO_3$ and brine. The organic layer is dried ($MgSO_4$) and concentrated under reduced pressure. The crude product is triturated twice with $Et_2O$ and dried in vacuo to provide (2S)-N-[2-(4-hydroxy-phenyl)-1-(4-phenyl-butylcarbamoyl)-ethyl]-benzamide which is used without further purification.

Step B: Bromo-[2-(1-methyl-1-phenyl-ethyl)-2H-tetrazol-5-yl]-acetic acid ethyl ester A solution of [2-(1-methyl-1-phenyl-ethyl)-2H-tetrazol-5-yl]-acetic acid ethyl ester (Norman, D. P. G. et al *JOC* 1999, 64, 9301–9306) (2.53 g, 9.23 mmol) in THF (50 mL) stirring at −78° C. under $N_2$ is treated with a 1 M soluion of NaHMDS in THF (9.23 mL) followed by NBS (1.64 g, 9.23 mmol). After 15 min, the reaction mixture is quenched by the slow addition of water and diluted with EtOAc. The organic layer is washed with water and brine, dried ($MgSO_4$) and concentrated under reduced pressure. The reaction mixture is purified by flash column chromatography eluted with 9:1 hexanes:EtOAc, then 2:1 hexanes:EtOAc, and finally flushed with EtOAc. The desired product, bromo-[2-(1-methyl-1-phenyl-ethyl)-2H-tetrazol-5-yl]-acetic acid ethyl ester, is recovered contaminated with 30% dibromide.

Step C: {4-[(2S)-2-Benzoylamino-2-(4-phenyl-butylcarbamoyl)-ethyl]-phenoxy}-[2-(1-methyl-1-phenyl-ethyl)-2H-tetrazol-5-yl]-acetic acid ethyl ester A solution of bromo-[2-(1-methyl-1-phenyl-ethyl)-2H-tetrazol-5-yl]-acetic acid ethyl ester of Step B (0.425 g, 1.208 mmol) in DMF (1 mL) is added to a stirred slurry of (2S)-N-[2-(4-hydroxy-phenyl)-1-(4-phenyl-butylcarbamoyl)-ethyl]-benzamide (step A) (0.201 g, 0.483 mmol) and $K_2CO_3$ (0.073 g, 0.53 mmol) in DMF (5 mL) at 0° C. under $N_2$. The reaction mixture is heated to 60° C. and stirred for 18 h. After cooling to RT, the reaction mixture is diluted with EtOAc and the organic layer washed with water (3×) and brine, dried ($MgSO_4$) and concentrated in vacuo. The reaction mixture is purified by flash column chromatography (1:1 hexanes/EtOAc) to provide {4-[(2S)-2-benzoylamino-2-(4-phenyl-butylcarbamoyl)-ethyl]-phenoxy}-[2-(1-methyl-1-phenyl-ethyl)-2H-tetrazol-5-yl]-acetic acid ethyl ester.

Step D: {4-[(2S)-2-Benzoylamino-2-(4-phenyl-butylcarbamoyl)-ethyl]-phenoxy}-[2-(1-methyl-1-phenyl-ethyl)-2H-tetrazol-5-yl]-acetic acid A solution of {4-[(2S)-2-benzoylamino-2-(4-phenyl-butylcarbamoyl)-ethyl]-phenoxy}-[2-(1methyl-1-phenyl-ethyl)-2H-tetrazol-5-yl]-acetic acid ethyl ester of Step C (0.070 g, 0.10 mmol) in EtOH (2 mL) is treated with 2 N NaOH (1 mL). After 1.5 h, the reaction is diluted with EtOAc, water and 10% HCl and the layers separated. The organic layer is washed with water and brine, dried ($MgSO_4$) and concentrated to provide {4-[(2S)-2-benzoylamino-2-(4-phenyl-butylcarbamoyl)-ethyl]-phenoxy}-[2-(1-methyl-1-phenyl-ethyl)-2H-tetrazol-5-yl]-acetic acid which is used without further purification.

Step E: {4-[(2S)-2-Benzoylamino-2-(4-phenyl-butylcarbamoyl)-ethyl]-phenoxy}-(2H-tetrazol-5-yl)-acetic acid 10% Pd/C (40 mg) is added to a stirred slurry of {4-[(2S)-2-benzoylamino-2-(4-phenyl-butylcarbamoyl)--ethyl]-phenoxy}-[2-(1-methyl-1-phenyl-ethyl)-2H-tetrazol-5- yl]-acetic acid of Step D (0.045 g, 0.068 mmol) and $HCO_2K$ (0.034 g, 0.409 mmol) in EtOH (2 mL). The reaction mixture is heated to reflux under $N_2$. After 5 h, the reaction mixture is cooled to RT and filtered to remove Pd/C. The filtrate is diluted with EtOAc, water and 10% HCl and the layers separated. The organic layer is washed with 10% HCl and brine, dried ($MgSO_4$) and concentrated under reduced pressure to provide {4-[(2S)-2-benzoylamino-2-(4-phenyl-butylcarbamoyl)-ethyl]-phenoxy}-(2H-tetrazol-5-yl )-acetic acid (compound 18); 1H NMR (400 MHz, acetone-$d_6$) δ7.82 (m, 3H), 7.45 (m, 4H), 7.19 (m, 7H), 6.99 (d, 2H), 6.36 (s, 1H), 4.81 (m, 1H), 3.21 (m, 3H), 3.05 (m, 1H) 2.58 (t, 2H), 1.59 (m, 2H), 1.48 (m, 2H); MS (ES+) m/z 543 (M+1); MS (ES−) m/z 541 (M−1).

The following compounds can be prepared using similar chemistry to that which is described above:

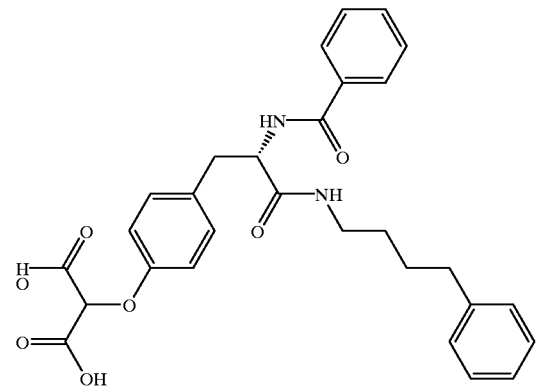

2-{4-[2-Benzoylamino-2-(4-phenyl-butylcarbamoyl)-ethyl]-phenoxy}-malonic acid (compound 19)

1H NMR (400 MHz, DMSO-$d_6$) δ8.46 (d, 1H), 8.00 (dd, 1H), 7.76 (d, 2H), 7.49 (dd, 1H), 7.41 (dd, 2H), 7.25–7.11 (m, 7H), 6.77 (d, 2H), 5.21 (s, 1H), 4.55 (m, 1H), 3.07 (m,

2H), 2.93 (m, 2H), 2.54 (dd, 2H), 1.51 (m, 2H), 1.40 (m, 2H); MS (ES+) m/z 519.2 (M+1); MS (ES−) m/z 517.2 (M−1).

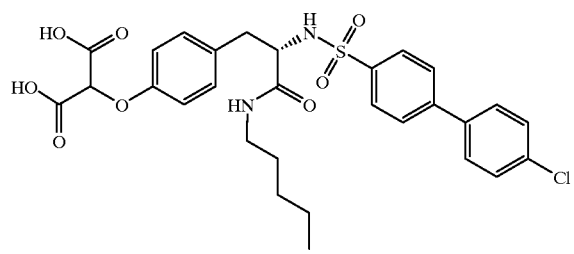

2-{4-[(2S)-2-(4′-Chloro-biphenyl-4-sulfonylamino)-2-pentylcarbamoyl-ethyl]-phenoxy}-malonic acid (compound 20)

MS (ES−) m/z 601 (M−1).

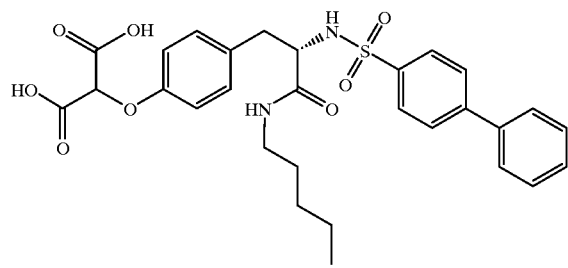

2-{4-[(2S)-2-(Biphenyl-4-sulfonylamino)-2-pentylcarbamoyl-ethyl]-phenoxy}-malonic acid (compound 21)

MS (ES−) m/z 567 (M−1).

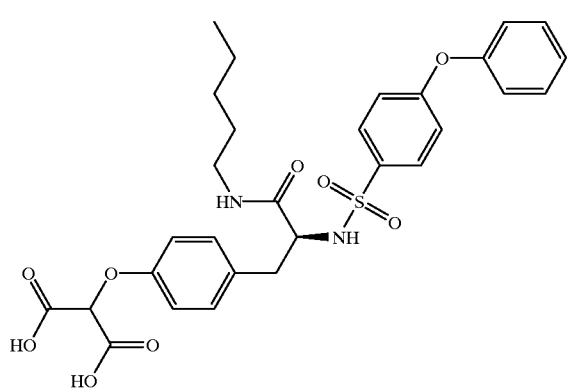

2-{4-[(2S)-2-Pentylcarbamoyl-2-(4-phenoxy-benzenesulfonylamino)-ethyl]-phenoxy}-malonic acid (compound 22)
MS (ES−) m/z 583.4 (M−1).

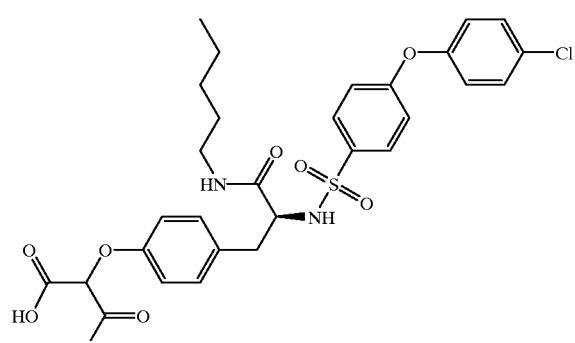

2-(4-{(2S)-2-[4-(4-Chloro-phenoxy)-benzenesulfonylamino]-2-pentylcarbamoyl-ethyl}-phenoxy)-malonic acid (compound 23)
MS (ES−) m/z 617 (M−1).

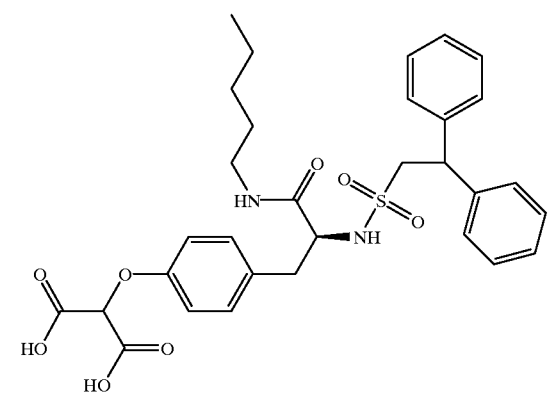

2-{4-[(2S)-2-(2,2-Diphenyl-ethanesulfonylamino)-2-pentylcarbamoyl-ethyl]-phenoxy}-malonic acid (compound 24)
MS (ES−) m/z 595 (M−1).

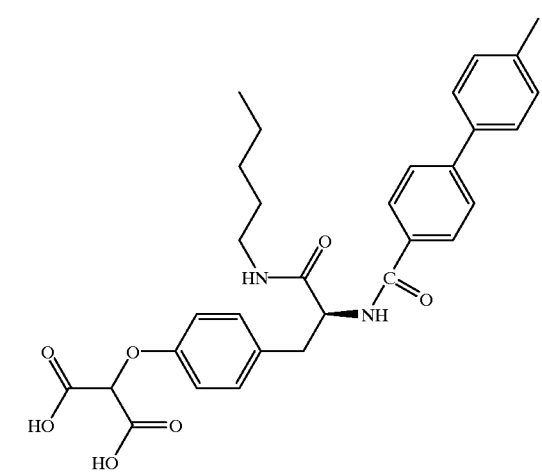

2-(4-{(2S)-2-[(4'-Methyl-biphenyl-4-carbonyl)-
amino]-2-pentylcarbamoyl-ethyl}-phenoxy)-malonic
acid (compound 25)
MS (ES−) m/z 545.7 (M−1).

2-{4-[(2S)-2-Benzenesulfonylamino-2-(4-phenyl-
butylcarbamoyl)-ethyl]-2-nitro-phenoxy}-malonic
acid (compound 28)
MS (ES+) m/z 600 (M+1).

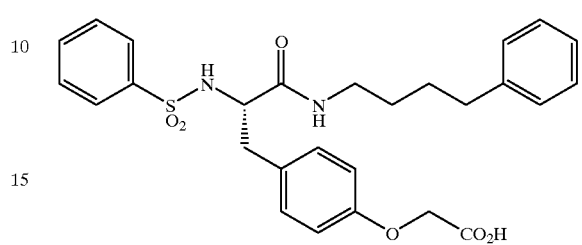

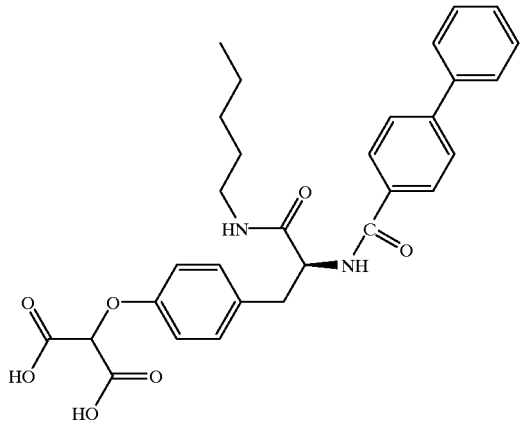

2-(4-{(2S)-2-[(Biphenyl-4-carbonyl)-amino]-2-
pentylcarbamoyl-ethyl}-phenoxy)-malonic acid
(compound 26)
MS (ES−) m/z 531.2 (M−1).

{4-[(2S)-2-Benzenesulfonylamino-2-(4-phenyl-
butylcarbamoyl)-ethyl]-phenoxy}-acetic acid
(compound 29)

$^1$H NMR (400 MHz, DMSO-$d_6$) δ12.9 (br, 1H), 8.02 (d, 1H), 7.81 (t, 1H), 7.16–7.58 (m, 10H), 6.99 (d, 2H), 6.73 (d, 2H), 4.59 (s, 2H), 3.82 (m, 1H), 2.69–2.79 (m, 4H), 2.56 (t, 2H), 1.43 (m, 2H), 1.18 (m, 2H); MS (ES−) m/z 509 (M−1).

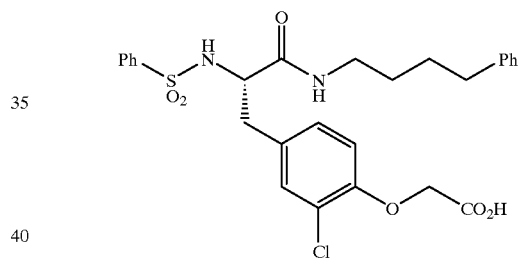

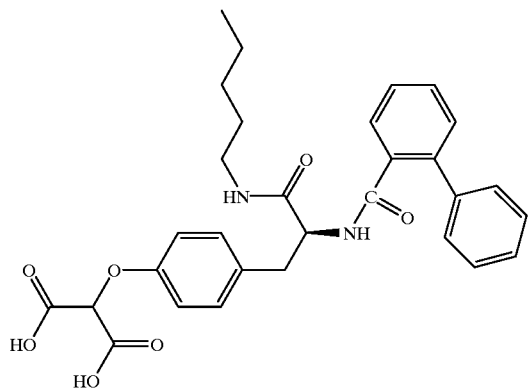

2-(4-{(2S)-2-[(Biphenyl-2-carbonyl)-amino]-2-
pentylcarbamoyl-ethyl}-phenoxy)-malonic acid
(compound 27)
MS (ES−) m/z 531.4 (M−1).

{4-[(2S)-2-Benzenesulfonylamino-2-(4-phenyl-
butylcarbamoyl)-ethyl]-2-chloro-phenoxy}-acetic
acid (compound 30)

$^1$H NMR (400 MHz, DMSO-$d_6$) δ12.9 (br, 1H), 8.02 (d, 1H), 7.81 (t, 1H), 7.12–7.53 (m, 12H), 6.96 (d, 1H), 6.81 (d, 1H), 4.7 (s, 2H), 3.81 (m, 1H), 2.82 (m, 2H), 2.67 (q, 2H), 2.56 (t, 2H), 1.41 (m, 2H), 1.22 (m, 2H); MS (ES−) m/z 543 (M−1).

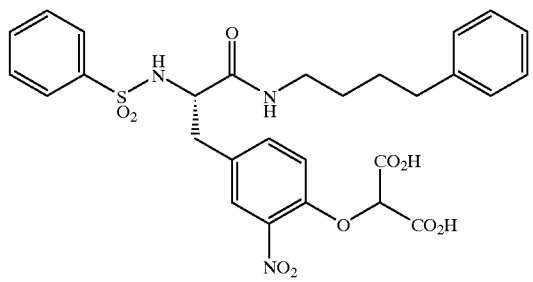

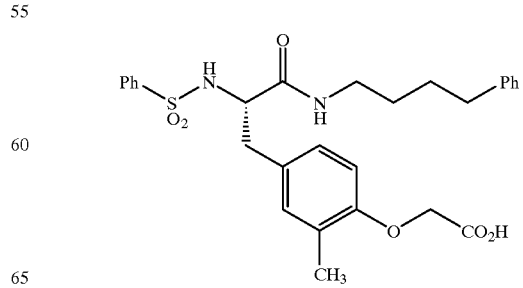

{4-[(2S)-2-Benzenesulfonylamino-2-(4-phenyl-butylcarbamoyl)-ethyl]-2-iodo-phenoxy}-acetic acid (compound 31)

¹H NMR (400 MHz, DMSO-d6) δ12.9 (br, 1H), 8.02 (d, 1H, 7.83 (t, 1H), 7.80 (m, 4H), 7.03–7.48 (m, 8H), 6.67 (d, 1H), 4.67 (s, 2H), 3.82 (m, 1H), 2.87 (m, 2H), 2.66 (q, 2H), 2.56 (t, 2H), 1.42 (m, 2H), 1.26 (m, 2H); MS (ES+) m/z 637 (M+1).

32

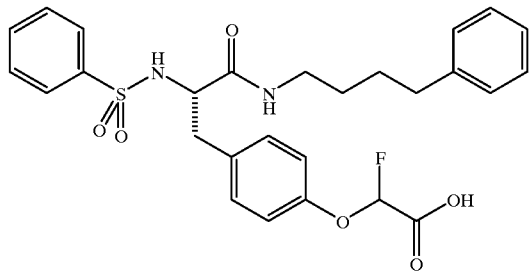

{4-[(2S)-2-Benzenesulfonylamino-2-(4-phenyl-butylcarbamoyl)-ethyl]-phenoxy}-fluoro-acetic acid (compound 32)

¹H NMR (400 MHz, DMSO-d₆) δ8.06 (d, 1H), 7.82 (bst, 1H), 7.59 (d, 2H), 7.51 (t, 1H), 7.40 (t, 2H), 7.28 (t, 2H), 7.18 (d, 3H), 7.11 (d, 2H), 6.95 (d, 2H), 6.30 (d, 1H), 3.84 (1H, q), 2.80 (m, 2H), 2.60 (m, 1H), 2.48 (m, 3H), 1.42 (m, 2H), 1.22 (m, 2H); MS (ES+) m/z 529 (M+1); MS (ES−) m/z 527 (M−1).

Example 3

33

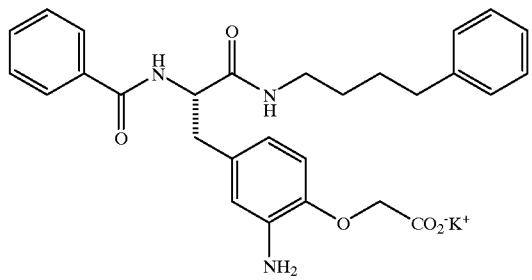

{2-Amino-4-[(2S)-2-benzoylamino-2-(4-phenyl-butylcarbamoyl)-ethyl]-phenoxy}-acetic acid, potassium salt (compound 33)

Step A: (2S)-2-tert-Butoxycarbonylamino-3-(4-hydroxy-3-nitro-phenyl)-propionic acid Nitro tyrosine (20.0 g, 88.4 mmol) is stirred with Na₂CO₃ (31.0 g, 292 mmol) in 1:1 dioxane:water (360 mL) for 15 min. BOC anhydride (21.2 g, 97.2 mmol) is added and stirring is continued for 14 h. The reaction mixture is diluted with water (1L) and extracted twice with Et₂O (2×250 mL). The aqueous phase is carefully acidified with concentrated HCl. The resulting yellow precipitate is collected by filtration and washed with water. The solid is dissolved in EtOAc (750 mL), washed with brine, dried (MgSO₄) and concentrated under reduced pressure to provide (2S)-2-tert-butoxycarbonylamino-3-(4-hydroxy-3-nitro-phenyl)-propionic acid as a yellow solid.

Step B: (2S)-[2-(4-Hydroxy-3-nitro-phenyl)-1-(4-phenyl-butylcarbamoyl)-ethyl]-carbamic acid tert-butyl ester (2S)-2-tert-Butoxycarbonylamino-3-(4-hydroxy-3-nitro-phenyl)-propionic acid of Step A (7.18 g, 22.0 mmol) is suspended in CH₂Cl₂ (320 mL) and cooled to 0° C. EDC (4.60 g, 24.0 mmol) and HOBt (3.67 g, 24.0 mmol) are added and the reaction mixture is stirred for 0.5 h. Phenyl butyl amine (3.8 mL, 24 mmol) is added dropwise and the reaction mixture is allowed to warm to RT. After stirring for 3 days, the reaction mixture is diluted with EtOAc (1L) and washed with 5% HCl, saturated NaHCO₃ and brine. The organic layer is dried (MgSO₄) and concentrated under reduced pressure. The crude product is recrystallized from CH₂Cl₂/hexanes to provide (2S)-[2-(4-hydroxy-3-nitro-phenyl)-1-(4-phenyl-butylcarbamoyl)-ethyl]-carbamic acid tert-butyl ester.

Step C: (2S)-2-Amino-3-(4-hydroxy-3-nitro-phenyl)-N-(4-phenyl-butyl)-propionamide HCl salt (2S)-[2-(4-Hydroxy-3-nitro-phenyl)-1-(4-phenyl-butylcarbamoyl)-ethyl]-carbamic acid tert-butyl ester of Step B (1.12 g, 2.40 mmol) is stirred in 4 N HCl in dioxane (20 mL) for 0.5 h. The volatiles are removed under reduced pressure and the resulting yellow residue triturated with Et₂O to give (2S)-2-amino-3-(4-hydroxy-3-nitro-phenyl)-N-(4-phenyl-butyl)-propionamide HCl salt as a hydroscopic solid.

Step D: (2S)-N-[2-(4-Hydroxy-3-nitro-phenyl)-1-(4-phenyl-butylcarbamoyl)-ethyl]-benzamide Hunig's base (0.048 mL, 0.27 mmol) followed by benzoyl chloride (0.016 mL, 0.14 mmol) are added to (2S)-2-amino-3-(4-hydroxy-3-nitro-phenyl)-N-(4-phenyl-butyl)-propionamide HCl salt of Step C (0.054 g, 0.137 mmol) stirring in CH₂Cl₂ (1 mL) under N₂. After 20 min, the reaction mixture is diluted with EtOAc and the organic layer is washed with saturated NaHCO₃, 10% HCl and brine. The organic layer is dried (MgSO₄) and concentrated under reduced pressure to give (2S)-N-[2-(4-hydroxy-3-nitro-phenyl)-1-(4-phenyl-butylcarbamoyl)-ethyl]-benzamide which is used without further purification.

Step E: {4-[(2S)-2-Benzoylamino-2-(4-phenyl-butylcarbamoyl)-ethyl]-2-nitro-phenoxy}-acetic acid ethyl ester A stirred solution of (2S)-N-[2-(4-hydroxy-3-nitro-phenyl)-1-(4-phenyl-butylcarbamoyl)-ethyl]-benzamide of Step D (0.133 g, 0.288 mmol) in DMF (5 mL) at 0° C. under N₂ is treated with K₂CO₃ (0.040 g, 0.29 mmol) followed by ethyl bromo acetate (0.032 mL, 0.29 mmol). The reaction mixture is allowed to warm to RT. After 18 h, the reaction mixture is diluted with water and EtOAc. The layers are separated and the organic layer is washed with water (3×) and brine. The organic layer is dried (MgSO₄) and concentrated under reduced pressure. The residue is purified by flash column chromatography (1:1 hexanes/EtOAc) to provide {4-[(2S)-2-benzoylamino-2-(4-phenyl-butylcarbamoyl)-ethyl]-2-nitro-phenoxy}-acetic acid ethyl ester.

Step F: {4-[(2S)-2-Benzoylamino-2-(4-phenyl-butylcarbamoyl)-ethyl]-2-nitro-phenoxy}-acetic acid A mixture of {4-[(2S)-2-benzoylamino-2-(4-phenyl-butylcarbamoyl)-ethyl]-2-nitro-phenoxy}-acetic acid ethyl ester of Step E (0.124 g, 0.226 mmol) in EtOH (2 mL) is treated with 0.5 mL of 2 N NaOH. After 1.5 h, the reaction is diluted with water, EtOAc, and 10% HCl. The layers are separated and the organic layer washed with water, and brine. The organic layer is dried (MgSO4) and concentrated under reduced pressure to provide {4-[(2S)-2-benzoylamino-2-(4-phenyl-butylcarbamoyl)-ethyl]-2-nitro-phenoxy}-acetic acid which is used without further purification.

Step G: {2-Amino-4-[(2S)-2-benzoylamino-2-(4-phenyl-butylcarbamoyl)-ethyl]-phenoxy}-acetic acid, potassium salt To a stirred slurry of {4-[(2S)-2-benzoylamino-2-(4-phenyl-butylcarbamoyl)-ethyl]-2-nitro-phenoxy}-acetic acid of Step F (0.095 g, 0.183 mmol) in EtOH (4 mL) is added $HCO_2K$ (0.092 g, 1.1 mmol) followed by 10% Pd/C (0.030 g). After 18 h, the reaction mixture is filtered through Celite, rinsed with MeOH and concentrated under reduced pressure. The crude product is purified by chromatography using a 10 g $C^{18}$ sep-pak column ($CH_3CN/H_2O$) to provide the title compound (compound 33), {2-amino-4-[(2S)-2-benzoylamino-2-(4-phenyl-butylcarbamoyl)-ethyl]-phenoxy}-acetic acid, potassium salt. $^1H$ NMR (400 MHz, DMSO-d6) δ8.39 (d, 1H), 7.97 (t, 1H), 7.80 (d, 2H), 7.43 (m, 3H), 7.20 (m, 5H), 6.51 (s, 1H), 6.48 (d, 1H), 6.38 (s, 1H), 4.91 (s, 2H), 4.51 (m, 1H), 3.91 (s, 2H), 3.08 (q, 2H), 2.82 (m, 2H), 2.56 (t, 2H), 1.54 (m, 2H), 1.40 (m, 2H); MS (ES+) m/z 490 (M+1).

The following compounds can be prepared using similar chemistry to that which is described above:

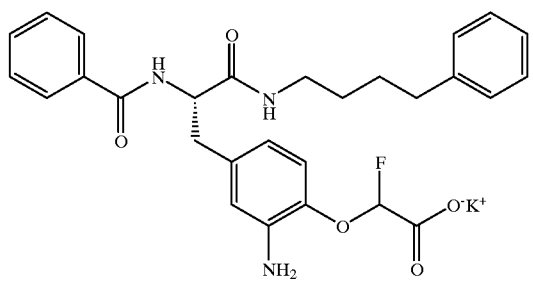

34

{2-Amino-4-[(2S)-2-benzoylamino-2-(4-phenyl-butylcarbamoyl)-ethyl]-phenoxy}-fluoro-acetic acid, potassium salt (compound 34)

$^1H$ NMR (400 MHz, DMSO-d6): δ8.46 (d, 1H), 7.95 (m, 1H), 7.79 (d, 2H), 7.48 (m, 1H), 7.42 (m, 2H), 7.22 (m, 2H), 7.16 (m, 3H), 6.73 (d, 1H), 6.57 (s, 1H), 6.38 (d, 1H), 5.26 (s, 2H), 5.10 (d, 1H), 4.52 (m, 1H), 3.06 (m, 2H), 2.84 (m, 2H), 2.48 (m, 2H), 1.50 (m, 2H), 1.38 (m, 2H); MS (ES+) m/z 508 (M-K+1).

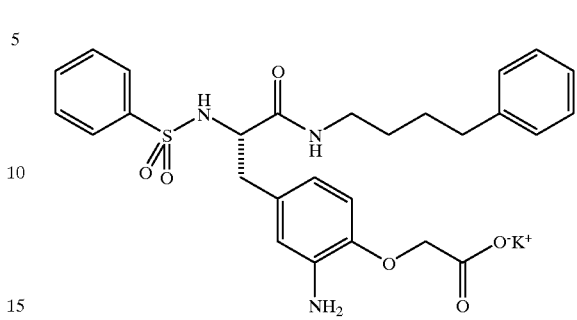

35

{2-Amino-4-[(2S)-2-benzenesulfonylamino-2-(4-phenyl-butylcarbamoyl)-ethyl]-phenoxy}-acetic acid, potassium salt (compound 35)

$^1H$ NMR (400 MHz, DMSO-d6) δ7.96 (bs, 1H), 7.78 (bs, 1H), 7.59 (d, 2H), 7.48 (m, 1H), 7.41 (t, 2H), 7.27 (t, 2H), 7.18 (m, 3H), 6.43 (d, 1H), 6.31 (s, 1H), 6.14 (d, 1H), 4.86 (s, 2H), 3.94 (s, 2H), 3.73 (m, 1H), 2.82 (m, 2H), 2.59 (m, 1H), 2.50 (m, 2H), 2.42 (m, 1H), 1.42 (m,2H), 1.20 (m, 2H); MS (ES+) m/z 526 (M-K+1); MS (ES−) m/z 524 ( M-K−1).

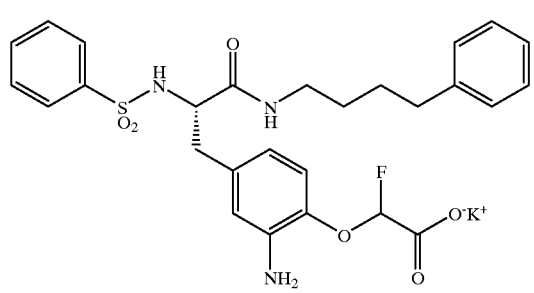

36

{2-Amino-4-[(2S)-2-benzenesulfonylamino-2-(4-phenyl-butylcarbamoyl)-ethyl]-phenoxy}-fluoro-acetic acid, potassium salt (compound 36)

$^1H$ NMR (400 MHz, DMSO-d6): δ7.74 (t, 1H), 7.53 (d, 2H), 7.45 (m, 1H), 7.37 (m, 2H), 7.25 (m, 2H), 7.16 (m, 3H), 6.65 (d, 1H), 6.39 (s, 1H), 6.15 (d, 1H), 5.20 (s, 2H), 5.11 (d, 1H), 3.74 (m, 1H), 3.31 (m, 2H), 2.79 (m, 2H), 2.57 (m, 2H), 1.38 (m, 2H), 1.16 (m, 2H); MS (ES+) m/z 544 (M-K+1).

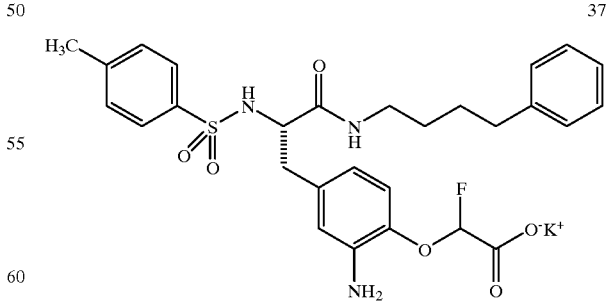

37

(2S)-{2-Amino-4-[2-(4-phenyl-butylcarbamoyl)-2-(toluene-4-sulfonylamino )-ethyl]-phenoxy}fluoro-acetic acid, potassium salt (compound 37)

$^1H$ NMR (400 MHz, DMSO-d6) δ7.72 (s, 1H), 7.45 (d, 2H), 7.27 (t, 2H), 7.18 (m, 5H), 6.65 (d, 1H), 6.40 (s, 1H), 6.16 (d, 1H), 5.17 (s, 2H), 5.10.5.12 (d, 1H), 3.65 (m, 1H), 2.85 (m, 2H), 251 (m, 4H), 2.29 (s, 3H), 1.42 (m, 2H), 1.20 (m, 2H); MS 558 (ES+) m/z (M+1).

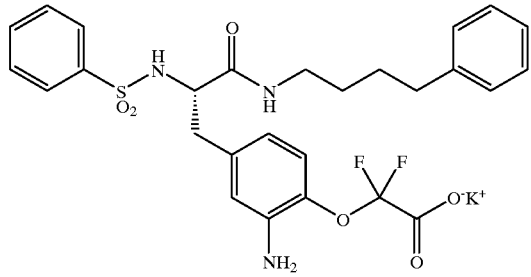

{2-Amino-4-[(2S)-2-benzenesulfonylamino-2-(4-phenyl-butylcarbamoyl)-ethyl]-phenoxy}-difluoro-acetic acid, potassium salt (compound 38)

$^1$H NMR (400 MHz, DMSO-d6) δ•• 7.75 (t, 1H), 7.58 (d, 2H), 7.48 (m, 1H), 7.38 (m, 2H), 7.24 (m, 2H), 7.15 (m, 3H), 6.71 (d, 1H), 6.39 (s, 1H), 6.16 (d, 1H), 4.92 (s, 2H), 3.76 (m, 1H), 3.31 (m, 2H), 2.76 (m, 2H), 2.60 (m, 2H), 1.37 (m, 2H), 1.15 (m, 2H); MS (ES+) m/z 562 (M-K+1).

Example 4

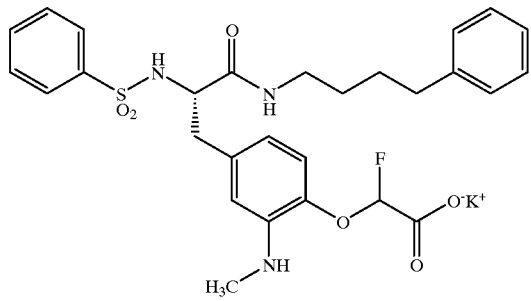

{4-[(2S)-2-Benzenesulfonylamino-2-(4-phenyl-butylcarbamoyl)-ethyl]-2-methylamino-phenoxy}-fluoro-acetic acid, potassium salt (compound 39)

Step A: (2S)-2-Benzenesulfonylamino-3-(4-hydroxy-3-methylamino-phenyl)-N-(4-phenyl-butyl)-propionamide (2S)-3-(3-Amino-4-hydroxy-phenyl)-2-benzenesulfonylamino-N-(4-phenyl-butyl)-propionamide (502 mg, 1.07 mmol) is dissolved in dichloroethane (5 mL). 37% formaldehyde (120 mg, 1.47 mmol) and NaBH(OAc)$_3$ (1.1 g, 5 mmol) are added. The mixture is stirred overnight. Saturated NaHCO$_3$ (20 mL) is added and the crude mixture is extracted with ETOAC three times. The organic phase is dried and concentrated in vacuo. The small volume of solution is filtered through silica gel plug to provide a crude solution of (2S)-2-benzenesulfonylamino-3-(4-hydroxy-3-methylamino-phenyl)-N-(4-phenyl-butyl)-propionamide which is used without further purification.

Step B: {5-[(2S)-2-Benzenesulfonylamino-2-(4-phenyl-butylcarbamoyl)-ethyl]-2-hydroxy-phenyl}-methyl-carbamic acid benzyl ester Crude (2S)-2-benzenesulfonylamino-3-(4-hydroxy-3-methylamino-phenyl)-N-(4-phenyl-butyl)-propionamide of Step A (170 mg, 0.35 mmol) is dissolved in pyridine (4 mL) and Cbz-Cl (60 μL, 0.40 mmol) is added at 0° C. The mixture is stirred at RT overnight. The solvent is removed by evaporation and the residue is dissolved in EtOAc and purified by column chromatography (hexane/EtOAc) to provide {5-[(2S)-2-benzenesulfonylamino-2-(4-phenyl-butylcarbamoyl)-ethyl]-2-hydroxy-phenyl}-methyl-carbamic acid benzyl ester.

Step C: [4-[(2S)-2-Benzenesulfonylamino-2-(4-phenyl-butylcarbamoyl)-ethyl]-2-(benzyloxycarbonyl-methyl-amino)-phenoxy]-fluoro-acetic acid ethyl ester {5-[(2S)-2-Benzenesulfonylamino-2-(4-phenyl-butylcarbamoyl)-ethyl]-2-hydroxy-phenyl}-methyl-carbamic acid benzyl ester of Step B (100 mg, 0.16 mmol) is dissolved in DMF (2 mL). Potassium carbonate (23 mg, 0.16 mmol) and bromo-fluoro-acetic acid ethyl ester (20 μl, 0.16 mmol) are added. The mixture is stirred at RT overnight. 40 μl (0.32 mmol) more of bromo-fluoro-acetic acid ethyl ester is added and stirred overnight. The mixture is purified through a silica plug to provide [4-[(2S)-2-benzenesulfonylamino-2-(4-phenyl-butylcarbamoyl)-ethyl]-2-(benzyloxycarbonyl-methyl-amino)-phenoxy]-fluoro-acetic acid ethyl ester which is used without further purification.

Step D: [4-[(2S)-2-Benzenesulfonylamino-2-(4-phenyl-butylcarbamoyl)-ethyl]-2-(benzyloxycarbonyl-methyl-amino)-phenoxy]-fluoro-acetic acid

[4-[(2S)-2-Benzenesulfonylamino-2-(4-phenyl-butylcarbamoyl)-ethyl]-2-(benzyloxycarbonyl-methyl-amino)-phenoxy]-fluoro-acetic acid ethyl ester of Step C is dissolved in EtOH (2 mL) and 1N KOH (0.32 mL) is added. The mixture is stirred overnight. The solution is concentrated, and suspended in ETOAC and loaded on silica gel plug. The plug is washed with ETOAC (100 mL) to remove the impurities. The product is eluted from the plug by using 2% HOAC in ETOAC. The filtrate is concentrated to provide [4-[(2S)-2-benzenesulfonylamino-2-(4-phenyl-butylcarbamoyl)-ethyl]-2-(benzyloxycarbonyl-methyl-amino)-phenoxy]-fluoro-acetic acid.

Step E: [4-[(2S)-2-Benzenesulfonylamino-2-(4-phenyl-butylcarbamoyl)-ethyl]-2-methylamino-phenoxy]6-fluoro-acetic acid, potassium salt

[4-[(2S)-2-Benzenesulfonylamino-2-(4-phenyl-butylcarbamoyl)-ethyl]-2-(benzyloxycarbonyl-methyl-amino)-phenoxy]-fluoro-acetic acid of Step D (78 mg, 0.11 mmol) is dissolved in ETOH (2 mL). Potassium formate (38 mg, 0.45 mmol), and Pd/C (10%, 10 mg) are added and stirred at RT overnight. The mixture is filtered through 0.45 μm Gelman Acrodisc. The filtrate is concentrated and purified by reverse phase chromatography (C$^{18}$ column, CH$_3$CN/H$_2$O) to provide the title compound (compound 39), {4-[(2S)-2-Benzenesulfonylamino-2-(4-phenyl-butylcarbamoyl)-ethyl]-2-methylamino-phenoxy}-fluoro-acetic acid, potassium salt. $^1$H NMR (400 MHz, DMSO-d6): δ7.79 (m, 1H), 7.55 (d, 2H), 7.46 (m, 1H), 7.37 (m, 2H), 7.25 (m, 2H), 7.14 (m, 3H), 6.68 (d, 1H), 6.23 (s, 1H), 6.18 (d, 1H), 6.08 (m, 1H), 5.20 (s, 2H), 5.10 (d, 1H), 3.74 (m, 1H), 2.84 (m, 2H), 2.64 (d, 3H), 2.50 (m, 2H), 1.41 (m, 2H), 1.21 (m, 2H); MS (ES+) m/z 558 (M-K+1).

Example 5

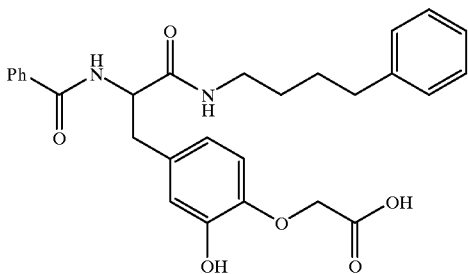

{4-[2-Benzoylamino-2-(4-phenyl-butylcarbamoyl)-ethyl]-2-hydroxy-phenoxy}-acetic acid (compound 40)

Step A: 3-Benzyloxy-4-hydroxybenzaldehyde 3,4-Dihydroxybenzaldehyde (30.2 g, 219 mmol) is dissolved in DMF (300 mL) and added to a suspension of NaH (60% oil, 17.2 g, 430 mmol) in DMF (500 mL) at RT. The mixture is stirred for 30 minutes and benzyl chloride (17.3 mL, 150 mmol) is added at 0° C. The reaction is stirred overnight. The solvent is removed by evaporation and the residue is dissolved in water (500 mL). The mixture is extracted three times with $CH_2Cl_2$. The aqueous layer is acidified with HOAC (100 mL). The product is precipitated and filtered, washed with water to provide 3-benzyloxy-4-hydroxybenzaldehyde.

Step B: N-[2-(3-Benzyloxy-4-hydroxy-phenyl)-1-(4-phenyl-butylcarbamoyl)-vinyl]-benzamide 3-Benzyloxy-4-hydroxybenzaldehyde of Step A (2.28 g, 10 mmol), hippuric acid (2.15 g, 12 mmol), and sodium acetate (1.07 g, 13 mmol) are mixed in acetic anhydride (15 mL, 159 mmol). The mixture is heated at 120° C. overnight. The reaction mixture is added to ice water (200 mL). The product is filtered, washed with 50% EtOH/water to provide crude azalactone. The intermediate is dried in vacuo and then dissolved in THF (20 mL) and 4-phenylbutyl amine (0.75 g, 5.0 mmol) is added. The reaction is stirred for 1 hour and the solvent is removed by evaporation. The residue is dissolved in THF (30 mL) and 1N NaOH (5.3 mL) is added and stirred overnight. The reaction is acidified with HOAC and poured into water to precipitate the product, N-[2-(3-benzyloxy-4-hydroxy-phenyl)-1-(4-phenyl-butylcarbamoyl)-vinyl]-benzamide.

Step C: {4-[2-Benzoylamino-2-(4-phenyl-butylcarbamoyl)-vinyl]-2-benzyloxy-phenoxy}-acetic acid tert-butyl ester N-[2-(3-benzyloxy-4-hydroxy-phenyl)-1-(4-phenyl-butylcarbamoyl)-vinyl]-benzamide of Step B (520 mg, 1.0 mmol) is dissolved in acetone (10 mL). $Cs_2CO_3$ (325 mg, 1.0 mmol) and t-butyl bromo acetate (0.18 mL, 1.1 mmol) are added and stirred for 2 hours at 50° C. The mixture is filtered through silica gel plug and washed with ETOAC. The filtrate is collected and concentrated. The product is precipitated from ethyl ether to provide {4-[2-benzoylamino-2-(4-phenyl-butylcarbamoyl)-vinyl]-2-benzyloxy-phenoxy}-acetic acid tert-butyl ester.

Step D: {4-[2-Benzoylamino-2-(4-phenyl-butylcarbamoyl)-ethyl]-2-hydroxy-phenoxy}-acetic acid {4-[2-Benzoylamino-2-(4-phenyl-butylcarbamoyl)-vinyl]-2-benzyloxy-phenoxy}-acetic acid tert-butyl ester of Step C (80 mg, 0.13 mmol) is dissolved in ETOH (2 mL) and $Pd(OH)_2$ (13 mg) on carbon is added. Hydrogen is applied and stirred overnight. The mixture is filtered through 0.45 μm Gelman Acrodisc and the filtrate is concentrated to oil. The oil is dissolved in TFA (2 mL). After 3 hours, the TFA is removed by evaporation. The crude material is purified by reverse phase chromatography ($C^{18}$, $CH_3CN/H_2O$) to provide the title compound (compound 40), {4-[2-benzoylamino-2-(4-phenyl-butylcarbamoyl)-ethyl]-2-hydroxy-phenoxy}-acetic acid; $^1H$ NMR (400 MHz, DMSO-d6): δ8.40 (d, 2H), 7.95 (t, 1H), 7.78 (d, 2H), 7.49 (m, 1H), 7.41 (m, 2H), 7.23 (m, 2H), 7.15 (m, 3H), 6.75 (s, 1H), 6.68 (d, 1H), 6.62 (d, 1H), 4.54 (m, 1H), 4.48 (s, 2H), 3.08 (m, 2H), 2.85 (m, 2H), 2.54 (m, 2H), 1.52 (m, 2H), 1.40 (m, 2H); MS (ES+) m/z 491 (M+1).

Example 6

The following compounds can be prepared essentially according to Schemes 1–5 and Examples 1–5:

(a) (2S)-N-[2-(4-Cyanomethoxy-phenyl)-1-(4-phenyl-butylcarbamoyl)-ethyl]-benzamide (compound 41);
(b) (2S)-2-Benzenesulfonylamino-3-(4-cyanomethoxy-phenyl)-N-(4-phenyl-butyl)-propionamide (compound 42);
(c) {2-Amino-4-[(2S)-2-benzenesulfonylamino-2-(3-phenoxy-propylcarbamoyl)-ethyl]-phenoxy}-fluoro-acetic acid (compound 43);
(d) {2-Amino-4-[(2S)-2-benzenesulfonylamino-2-(2-benzyloxy-ethylcarbamoyl)-ethyl]-phenoxy}-fluoro-acetic acid (compound 44);
(e) (2-Amino-4-{(2S)-2-benzenesulfonylamino-2-[4-(3-trifluoromethyl-phenyl)-butylcarbamoyl]-ethyl}-phenoxy)-fluoro-acetic acid (compound 45);
(f) (2-Amino-4-{(2S)-2-benzenesulfonylamino-2-[4-(4-trifluoromethyl-phenyl)-butylcarbamoyl]-ethyl}-phenoxy)-fluoro-acetic acid (compound 46);
(g) (2-Amino-4-{(2S)-2-benzenesulfonylamino-2-[4-(2-trifluoromethyl-phenyl)-butylcarbamoyl]-ethyl}-phenoxy)-fluoro-acetic acid (compound 47);
(h) (2-Amino-4-{(2S)-2-benzenesulfonylamino-2-[4-(3-methoxy-phenyl)-butylcarbamoyl]-ethyl}-phenoxy)-fluoro-acetic acid (compound 48);
(i) (2-Amino-4-{(2S)-2-benzenesulfonylamino-2-[4-(4-methoxy-phenyl)-butylcarbamoyl]-ethyl}-phenoxy)-fluoro-acetic acid (compound 49);
(j) (2-Amino-4-{(2S)-2-benzenesulfonylamino-2-[4-(2-methoxy-phenyl)-butylcarbamoyl]-ethyl}-phenoxy)-fluoro-acetic acid (compound 50);
(k) {2-Amino-4-[(2S)-2-methanesulfonylamino-2-(4-phenyl-butylcarbamoyl)-ethyl]-phenoxy}-fluoro-acetic acid (compound 51);
(l) {2-Amino-4-[(2S)-2-(4-phenyl-butylcarbamoyl)-2-phenylmethanesulfonylamino-ethyl]-phenoxy}-fluoro-acetic acid (compound 52);
(m) {2-Amino-4-[(2S)-2-(4-phenyl-butylcarbamoyl)-2-(3-phenyl-propionylamino)-ethyl]-phenoxy}-fluoro-acetic acid (compound 53);
(n) {2-Amino-4-[(2S)-2-phenylacetylamino-2-(4-phenyl-butylcarbamoyl)-ethyl]-phenoxy}-fluoro-acetic acid (compound 54); and
(o) {2-Amino-4-[(2S)-2-(cyclohexanecarbonyl-amino)-2-(4-phenyl-butylcarbamoyl)-ethyl]-phenoxy}-fluoro-acetic acid (compound 55).

Example 7

Biological Assays

CDC25A Assay

1×Assay Buffer: 30 mM Tris, pH 8.5; 75 mM NaCl; 0.67 mM EDTA; 0.033% bovine serum albumin (BSA); and 10 mM DTT.

Fluorescein Diphosphate (FDP) substrate: 5 mg FDP is reconstituted in 890 μl 10 mM Tris, pH 7.0–8.0 to make 10 mM stock. Aliquot and freeze at −20° C. until use.

Stock is diluted to 200 μM working stock (50×dilution). The assay requires 10 μl FDP per well.

Human recombinant CDC25A: Human recombinant CDC25A is cloned, expressed and purified. In the absence of well-characterized specific protein concentration or active site calculations, enzyme content is normalized across lots according to enzyme activity. The enzyme activity is linear over the duration of the assay, and the total relative fluorescence units (RFUs) generated should not exceed 10% of theoretical maximum. At 20 μM FDP in the assay, the signal should not exceed 25,000 RFUs over the duration of the assay.

Procedure: Polypropylene assay plates are labeled accordingly. 25 μl 100 μM test compound is added to the corresponding well of the assay plate. 55 μl of assay buffer is then added to each well, followed by 10 μl 200 μM FDP. The reaction is then initiated with the addition of 10 μl of 10×CDC25A. The cells are incubated for an hour and the reaction is subsequently terminated by addition of 10 μl stop solution (0.5 M NaOH/50% ETOH). Fluorescence is read at ex485/em538/cutoff 530.

PTP1B Assay

1×Assay Buffer: 50 mM ADA (N-[2-Acetamido]-2-iminodiacetic acid; N-[Carbamoylmethyl]iminodiacetic acid), pH 6.0; 1 mM EDTA; 10 mM DTT; 0.1% TritonX.

Fluorescein Diphosphate (FDP) substrate: 5 mg FDP is reconstituted in 890 μl 10 mM Tris, pH 7.0–8.0 to make 10 mM stock. Aliquot and freeze at −20° C. until use.

Stock is diluted to 200 μM working stock in assay buffer (50×dilution). The assay requires 10 μl FDP per well.

Human recombinant PTP1B: Human recombinant PTP1B is cloned, expressed, and purified. In the absence of well-characterized specific protein concentration or active site calculations, enzyme content is normalized across lots according to enzyme activity. The enzyme activity is linear over the duration of the assay, and the total relative fluorescence units (RFUs) generated should not exceed 10% of theoretical maximum. At 20 μM FDP in the assay, the signal should not exceed 11,000 RFUs over the duration of the assay. Quantum yield (fluorescence per unit fluorophore) is decreased at pH 6.0.

Procedure: Polypropylene assay plates are labeled accordingly. 25 μl 100 μM test compound is added to the corresponding well of the assay plate. 55 μl of assay buffer is then added to each well, followed by 10 μl 200 μM FDP. The reaction is then initiated with the addition of 10 μl of 10×PTB1B. The cells are incubated for 30 minutes and the reaction is subsequently terminated by addition of 10 μl stop solution (0.5 M NaOH/50% ETOH). Fluorescence is read at ex485/em538/cutoff 530.

The compounds of Examples 1–5 are tested for their activity in the CDC25A and PTP-1B enzymes according to the procedures described above. The results are measured as Ki values (μM) in both assays and range from about between 0.01 μM to 1000 μM.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

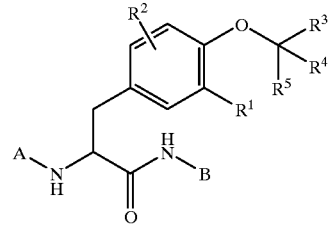

and pharmaceutically acceptable salts and prodrugs thereof, wherein $R^1$ is selected from hydrogen, hydroxy, halogen, amino, monoalkylamino, trifluoromethyl, aminomethyl, cyano, nitro, and —COOR$^6$;

$R^2$ is selected from hydrogen, hydroxy, halogen, lower alkyl, lower alkoxy, alkoxyalkyl, hydroxyalkyl, lower alkenyl, amino, mono- or dialkylamino, cyano, nitro, trifluromethyl, —CON(R$^6$)$_2$, and —COOR$^6$;

$R^3$, $R^4$, $R^5$ are independently selected from hydrogen, hydroxy, halogen, lower alkyl, lower alkenyl, cycloalkyl, cyano, —CON(R$^6$)$_2$, —COOR$^6$, and aryl optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

A is selected from —S(O)$_2$R$^7$ or —(CH$_2$)$_n$S(O)$_q$R$^7$;

B is selected from hydrogen, lower alkyl, lower alkenyl, lower alkynyl, —(CH$_2$)$_p$S((O)$_q$R$^7$, —(CH$_2$)$_p$C(O)R$^7$, —(CH$_2$)$_p$C(O)NHR$^7$, —(CH$_2$)$_p$CO$_2$R$^7$, (CH$_2$)$_n$OR$^7$, and aryl, arylalkyl, arylalkenyl and arylalkynyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

n is 2–4;

p is 1–2;

q is 0–2;

$R^6$ is selected from hydrogen, lower alkyl, and lower alkenyl;

$R^7$ is selected from lower alkyl, or aryl and arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$; and $R^8$ is independently selected from hydrogen, and lower alkyl and aryl optionally substituted with one, two or three groups independently selected from lower alkyl, halogen, lower alkoxy, hydroxy, amino, mono- or dialkylamino, and trifluoromethyl.

2. A compound according to claim 1 wherein $R^1$ is selected from hydroxy, amino, monoalkylamino, and nitro;

$R^2$ is selected from hydrogen, hydroxy, halogen, lower alkyl, lower alkoxy, alkoxyalkyl, hydroxyalkyl, lower alkenyl, amino, mono- or dialkylamino, cyano, nitro, trifluromethyl and —CON($R^6$)$_2$;

$R^3$ is selected from hydrogen, fluoro and methyl;

$R^4$ is selected from hydrogen; and $R^5$ is —COOH.

3. A compound according to claim 1 wherein $R^1$ is selected from hydroxy, amino, mono-$C_{1-2}$-alkylamino and —COOH;

$R^2$ is hydrogen;

$R^3$ is selected from hydrogen, fluoro and methyl;

$R^4$ is selected from hydrogen and —COOH;

$R^5$ is —COOH;

A is —S(O)$_2$R$^7$;

B is selected from lower alkyl, —(CH$_2$)$_n$OR$^7$, and aryl-$C_{2-6}$-alkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

$R^7$ is selected from aryl and aryl-$C_{1-3}$-alkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

n is 2–4; and $R^8$ is lower alkyl.

4. A compound according to claim 1 wherein $R^1$ is selected from hydroxy, amino, and methylamino;

$R^2$ is hydrogen;

$R^3$ is selected from hydrogen and fluoro;

$R^4$ is hydrogen;

$R^5$ is —COOH;

A is —S(O)$_2$R$^7$;

B is selected from $C_{4-6}$-alkyl, —(CH$_2$)$_n$OR$^7$, and phenyl-$C_{3-4}$-alkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

$R^7$ is selected from phenyl and phenyl-$C_{1-2}$-alkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

n is 2–4;

and R is lower alkyl.

5. A compound according to claim 1 wherein wherein $R^3$ is selected from hydrogen, hydroxy, halogen, lower alkyl, lower alkenyl, cycloalkyl, cyano, —CON(R$^6$)$_2$ and —COOR$^6$, and aryl optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

$R^4$ is hydrogen; and $R^5$ is —CO$_2$H.

6. A compound according to claim 1 wherein $R^1$ is selected from amino and hydroxy;

$R^2$ is hydrogen;

$R^3$ is selected from hydrogen, fluoro and methyl;

$R^4$ is hydrogen;

$R^5$ is —CO$_2$H;

A is —S(O)$_2$R$^7$;

B is selected from (CH$_2$)$_n$OR$^7$, and arylalkyl, where the ring portion of each is optionally substituted with one, two or three groups independently selected from halogen, lower alkyl, hydroxy, amino, mono- or dialkylamino, trifluoromethyl, —C(O)R$^8$, COOR$^8$, —C(O)NHR$^8$, and —OR$^8$;

$R^7$ is selected from aryl and arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$; and n is 2–4.

7. A compound according to claim 1 wherein $R^1$ is —CO$_2$H;

$R^3$ hydrogen;

$R^4$ is hydrogen; and $R^5$ is —COO$_2$H.

8. A compound according to claim 1 wherein $R^1$—CO$_2$H;

$R^2$ is hydrogen;

$R^3$ is hydrogen;

$R^4$ is hydrogen;

$R^5$ is —CO$_2$H;

A is —S(O)$_2$R$^7$;

B is selected from —(CH$_2$)$_n$OR$^7$, and arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

$R^7$ is selected from aryl and arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$; and n is 2–4.

9. A compound according to claim 1 wherein $R^1$ is hydrogen;

$R^3$ is hydrogen;

$R^4$ is selected from hydrogen, halogen, lower alkyl, lower alkenyl, cycloalkyl, cyano, —CON(R$^6$)$_2$, —COOR$^6$, and aryl optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$; and $R^5$ is —COO$_2$H.

10. A compound according to claim 1 wherein $R^2$ is hydrogen;

$R^4$ is selected from —COOH and tetrazolyl;

A is —S(O)$_2$R$^7$;

B is selected from —(CH$_2$)$_n$OR$^7$, and
arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$;

R$^7$ is selected from aryl and arylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$, and —OR$^8$; and n is 2–4.

11. A compound according to claim 1 which is selected from:

5-[(2S)-2-benzenesulfonylamino-2-(4-methoxy-benzylcarbamoyl)-ethyl]-2-carboxymethoxy-benzoic acid;

5-((2S)-2-benzenesulfonylamino-2-pentylcarbamoyl-ethyl)-2-carboxymethoxy-benzoic acid;

2-carboxymethoxy-5-((2S)-2-pentylcarbamoyl-2-phenylmethanesulfonylamino-ethyl)-benzoic acid;

5-[(2S)-2-benzenesulfonylamino-2-(3-methoxy-propylcarbamoyl)-ethyl]-2-carboxymethoxy-benzoic acid;

5-{(2S)-2-benzenesulfonylamino-2-[2-(4-methoxy-phenyl)-ethylcarbamoyl]-ethyl}-2-carboxymethoxy-benzoic acid;

5-[(2S)-2-benzenesulfonylamino-2-(4-phenyl-butylcarbamoyl)-ethyl]-2-carboxymethoxy-benzoic acid;

5-[(2S)-2-(biphenyl-4-sulfonylamino)-2-(4-phenyl-butylcarbamoyl)-ethyl]-2-carboxymethoxy-benzoic acid;

5-{(2S)-2-benzenesulfonylamino-2-[3-(4-methoxy-phenyl)-propylcarbamoyl]-ethyl}-2-carboxymethoxy-benzoic acid;

5-{(2S)-2-benzenesulfonylamino-2-[3-(4-methoxy-phenoxy)-propylcarbamoyl]-ethyl}-2-carboxymethoxy-benzoic acid;

5-((2S)-2-benzenesulfonylamino-2-phenethylcarbamoyl-ethyl)-2-carboxymethoxy-benzoic acid;

5-[(2S)-2-benzenesulfonylamino-2-(3-phenyl-propylcarbamoyl)-ethyl]-2-carboxymethoxy-benzoic acid;

5-[(2S)-2-benzenesulfonylamino-2-(3,3-diphenyl-propylcarbamoyl)-ethyl]-2-carboxymethoxy-benzoic acid;

2-{4-[(2S)-2-(4'-chloro-biphenyl-4-sulfonylamino)-2-pentylcarbamoyl-ethyl]-phenoxy}-malonic acid;

2-{4-[(2S)-2-(biphenyl-4-sulfonylamino)-2-pentylcarbamoyl-ethyl]-phenoxy}-malonic acid;

2-{4-[(2S)-2-pentylcarbamoyl-2-(4-phenoxy-benzenesulfonylamino)-ethyl]-phenoxy}-malonic acid;

2-(4-{(2S)-2-[4-(4-Chloro-phenoxy)-benzenesulfonylamino]-2-pentylcarbamoyl-ethyl}-phenoxy)-malonic acid;

2-{4-[(2S)-2-(2,2-diphenyl-ethanesulfonylamino)-2-pentylcarbamoyl-ethyl]-phenoxy}-malonic acid;

2-{4-[(2S)-2-benzenesulfonylamino-2-(4-phenyl-butylcarbamoyl)-ethyl]-2-nitro-phenoxy}-malonic acid;

{4-[(2S)-2-benzenesulfonylamino-2-(4-phenyl-butylcarbamoyl)-ethyl]-phenoxy}-acetic acid;

{4-[(2S)-2-benzenesulfonylamino-2-(4-phenyl-butylcarbamoyl)-ethyl]-2-chloro-phenoxy}-acetic acid;

{4-[(2S)-2-benzenesulfonylamino-2-(4-phenyl-butylcarbamoyl)-ethyl]-2-iodo-phenoxy}-acetic acid;

{4-[(2S)-2-benzenesulfonylamino-2-(4-phenyl-butylcarbamoyl)ethyl]-phenoxy}-fluoro-acetic acid;

{2-amino-4-[(2S)-2-benzenesulfonylamino-2-(4-phenyl-butylcarbamoyl)-ethyl]-phenoxy}-acetic acid;

{2-amino-4-[(2S)-2-benzenesulfonylamino-2-(4-phenyl-butylcarbamoyl)-ethyl]-phenoxy}-fluoro-acetic acid;

(2S)-{2-amino-4-[2-(4-phenyl-butylcarbamoyl)-2-(toluene-4-sulfonylamino)-ethyl]-phenoxy}-fluoro-acetic acid;

{2-amino-4-[(2S)-2-benzenesulfonylamino-2-(4-phenyl-butylcarbamoyl)-ethyl]-phenoxy}-difluoro-acetic acid;

{4-[(2S)-2-benzenesulfonylamino-2-(4-phenyl-butylcarbamoyl)-ethyl]-2-methylamino-phenoxy}-fluoro-acetic acid;

(2S)-2-benzenesulfonylamino-3-(4-cyanomethoxy-phenyl)-N-(4-phenyl-butyl)-propionamide;

{2-amino-4-[(2S)-2-benzenesulfonylamino-2-(3-phenoxy-propylcarbamoyl)-ethyl]-phenoxy}-fluoro-acetic acid;

{2-amino-4-[(2S)-2-benzenesulfonylamino-2-(2-benzyloxy-ethylcarbamoyl)-ethyl]-phenoxy}-fluoro-acetic acid;

(2-amino-4-{(2S)-2-benzenesulfonylamino-2-[4-(3-trifluoromethyl-phenyl)-butylcarbamoyl]-ethyl}-phenoxy)-fluoro-acetic acid;

(2-amino-4-{(2S)-2-benzenesulfonylamino-2-[4-(4-trifluoromethyl-phenyl)-butylcarbamoyl]-ethyl}-phenoxy)-fluoro-acetic acid;

(2-amino-4-{(2S)-2-benzenesulfonylamino-2-[4-(2-trifluoromethyl-phenyl)-butylcarbamoyl]-ethyl}-phenoxy)-fluoro-acetic acid;

(2-amino-4-{(2S)-2-benzenesulfonylamino-2-[4-(3-methoxy-phenyl)-butylcarbamoyl]-ethyl}-phenoxy)-fluoro-acetic acid;

(2-amino-4-{(2S)-2-benzenesulfonylamino-2-[4-(4-methoxy-phenyl)-butylcarbamoyl]ethyl}-phenoxy)-fluoro-acetic acid;

(2-amino-4-{(2S)-2-benzenesulfonylamino-2-[4-(2-methoxy-phenyl)-butylcarbamoyl]-ethyl}-phenoxy)-fluoro-acetic acid;

{2-amino-4-[(2S)-2-methanesulfonylamino-2-(4-phenyl-butylcarbamoyl)-ethyl]-phenoxy}-fluoro-acetic acid;

{2-amino-4-[(2S)-2-(4-phenyl-butylcarbamoyl)-2-phenylmethanesulfonylamino-ethyl]-phenoxy}-fluoro-acetic acid;

{2-amino-4-[(2S)-2-(4-phenyl-butylcarbamoyl)-2-(3-phenyl-propionylamino)-ethyl]-phenoxy}-fluoro-acetic acid;

{2-amino-4-[(2S)-2-phenylacetylamino-2-(4-phenyl-butylcarbamoyl)-ethyl]-phenoxy}-fluoro-acetic acid; and {2-amino-4-[(2S)-2-(cyclohexanecarbonyl-amino)-2-(4-phenyl-butylcarbamoyl)-ethyl]-phenoxy}-fluoro-acetic acid; or pharmaceutically acceptable salts and prodrugs thereof.

12. A pharmaceutical formulation comprising a compound according to claim 1 and a pharmaceutically acceptable carrier.

13. A method of treating Type II Diabetes Mellitus in a patient in need thereof comprising administering to the patient a therapeutically effective amount of the compound according to claim 1.

14. A method of inhibiting tyrosine phosphatase activity in a mammal comprising administration of an effective amount of a compound of claim 1 to said mammal.

15. A method of inhibiting PTP-B1 activity in a mammal comprising administration of an effective amount of a compound of claim 1 to said mammal.

16. A method of inhibiting CDC25A activity in a mammal comprising administration of an effective amount of a compound of claim 1 to said mammal.

* * * * *